United States Patent
Zhu et al.

(10) Patent No.: US 11,649,286 B2
(45) Date of Patent: May 16, 2023

(54) TRI-SPECIFIC ANTIBODIES

(71) Applicants: SYSTIMMUNE, INC., Redmond, WA (US); SICHUAN BAILI PHARMACEUTICAL CO. LTD., Chengdu (CN)

(72) Inventors: Yi Zhu, Chengdu (CN); Ole Olsen, Everett, WA (US); Dong Xia, Redmond, WA (US); David Jellyman, Duvall, WA (US); Katrina Bykova, Seattle, WA (US); Anne-Marie K. Rousseau, Seattle, WA (US); Bill Brady, Bothell, WA (US); Blair Renshaw, Renton, WA (US); Brian Kovacevich, Snohomish, WA (US); Yu Liang, Redmond, WA (US); Zeren Gao, Redmond, WA (US)

(73) Assignees: SYSTIMMUNE INC., Redmond, WA (US); BAILI-BIO (CHENGDU) PHARMACEUTICAL CO., LTD., Chengdu (CN)

( * ) Notice: Subject to any disclaimer, the term of this patent is extended or adjusted under 35 U.S.C. 154(b) by 359 days.

(21) Appl. No.: 16/615,117

(22) PCT Filed: Jun. 22, 2018

(86) PCT No.: PCT/US2018/039153
§ 371 (c)(1),
(2) Date: Nov. 19, 2019

(87) PCT Pub. No.: WO2019/005637
PCT Pub. Date: Jan. 3, 2019

(65) Prior Publication Data
US 2020/0157213 A1    May 21, 2020

Related U.S. Application Data

(60) Provisional application No. 62/524,554, filed on Jun. 25, 2017.

(51) Int. Cl.
| | | |
|---|---|---|
| *C07K 16/28* | (2006.01) | |
| *A61K 39/395* | (2006.01) | |
| *A61K 47/68* | (2017.01) | |
| *A61K 45/06* | (2006.01) | |

(52) U.S. Cl.
CPC ...... *C07K 16/2803* (2013.01); *A61K 39/3955* (2013.01); *A61K 45/06* (2013.01); *A61K 47/6803* (2017.08); *C07K 16/2809* (2013.01); *C07K 16/2827* (2013.01); *C07K 16/2863* (2013.01); *C07K 2317/31* (2013.01); *C07K 2317/55* (2013.01); *C07K 2317/622* (2013.01); *C07K 2317/73* (2013.01)

(58) Field of Classification Search
CPC ............. C07K 16/2863; C07K 16/468; C07K 2317/31; C07K 16/2809; C07K 2317/622; C07K 2317/55
See application file for complete search history.

(56) References Cited

FOREIGN PATENT DOCUMENTS

| WO | WO2014167022 | * | 10/2014 | ............ C07K 16/28 |
| WO | WO2017019894 | * | 2/2017 | ............ C07K 16/28 |

OTHER PUBLICATIONS

Lloyd et al., Protein Engineering, Design & Selection 22,159-168,2009. (Year: 2009).*
Giusti et al. PNAS, 84, 2926-2930, 1987. (Year: 1987).*

* cited by examiner

*Primary Examiner* — Elly-Gerald Stoica
(74) *Attorney, Agent, or Firm* — Feng Wan

(57) ABSTRACT

The application provides tri-specific antibody monomers having a N-terminal and a C-terminal, comprising in tandem from the N-terminal to the C-terminal, a first scFv domain at the N-terminal, a Fab domain, a Fc domain, and a second scFv domain at the C-terminal. In one embodiment, the first scFv domain, the Fab domain, and the second scFv domain each has a binding specificity against a different antigen.

17 Claims, 11 Drawing Sheets
Specification includes a Sequence Listing.

MULTI-SPECIFIC ANTIBODIES AND METHODS OF MAKING AND USING THEREOF

FIGURE 1 shows the example tri-specific antibodies used in binding and RTCC assays

| Antibody ID | Domain 1 LH-scFv | Humanized Variant | Domain 2 LH-scFv | Humanized Variant | IgG Fc | Domain 3 HL-scFv | Humanized Variant |
|---|---|---|---|---|---|---|---|
| SI-27X33 | R11 | - | 4420(FITC) | - | n2 | I2C | - |
| SI-27X39 | 323H7 | L1H4 | PL230C6 | H3L2 | n2 | I2C | - |
| SI-27X45 | 338H4 | L4H3 | PL230C6 | H3L2 | n2 | PL221 | H1L1 |
| SI-27X62 | R11 | - | PL230C6 | H3L2 | n2 | 4420(FITC) | - |
| SI-27X63 | 323H7 | L1H4 | PL230C6 | H3L2 | n2 | 284A10 | H1L1 |
| SI-27X69 | 338H4 | L4H3 | PL230C6 | H3L2 | n2 | 299F6 | H2L1 |
| SI-27X73 | 338H4 | L4H3 | PL230C6 | H3L2 | n2 | 480C8 | H2L1 |
| SI-27X75 | 4420(FITC) | - | PL230C6 | H3L2 | n2 | I2C | - |
| SI-27X109 | PL230C6 | L2H3 | 4420(FITC) | - | n2 | 480C8 | H2L1 |
| SI-37X1 | PL230C6 | L2H3 | 806 | - | n2 | 480C8 | H2L1 |
| SI-37X2 | 806 | - | PL230C6 | H3L2 | n2 | 480C8 | H2L1 |
| SI-37X3 | 4420(FITC) | - | 806 | - | n2 | 480C8 | H2L1 |
| SI-37X4 | PL230C6 | L2H3 | 806 | - | n2 | 4420(FITC) | - |
| SI-37X5 | 806 | - | 4420(FITC) | - | n2 | 480C8 | H2L1 |
| SI-37X6 | 806 | - | PL230C6 | H3L2 | n2 | 4420(FITC) | H2L1 |
| SI-37X7 | - | - | - | - | n2 | 480C8 | H2L1 |
| SI-34X2 | 21D4 | - | PL230C6 | H3L2 | n2 | 480C8 | H2L1 |
| SI-34X7 | 4420(FITC) | - | PL230C6 | H3L2 | n2 | 480C8 | H2L1 |
| SI-34X8 | 21D4 | - | 4420(FITC) | - | n2 | 480C8 | H2L1 |
| SI-34X9 | 21D4 | - | PL230C6 | H3L2 | n2 | 4420(FITC) | - |

MULTI-SPECIFIC ANTIBODIES AND METHODS OF MAKING AND USING THEREOF

FIGURE 2 shows the specificity of the antibody binding domains used in the example tri-specific antibodies

| Antibody Name | Specificity |
|---|---|
| 21D4 | CD19 |
| 806 | EGFRviii |
| 4420 | FITC |
| R11 | ROR1 Kringle Domain |
| 323H7 | ROR1 IgD Domain |
| 338H4 | ROR1 Frizzled Domain |
| PL230C6 | PD-L1 |
| I2C | CD3 complex Epsilon chain |
| 284A10 | CD3 complex Epsilon chain |
| 299F6 | CD3 complex Epsilon chain |
| 480C8 | CD3 complex Epsilon chain |

MULTI-SPECIFIC ANTIBODIES AND METHODS OF MAKING AND USING THEREOF
FIGURE 3 is a diagram showing a symmetric tri-specific antibody according to at least one embodiment.
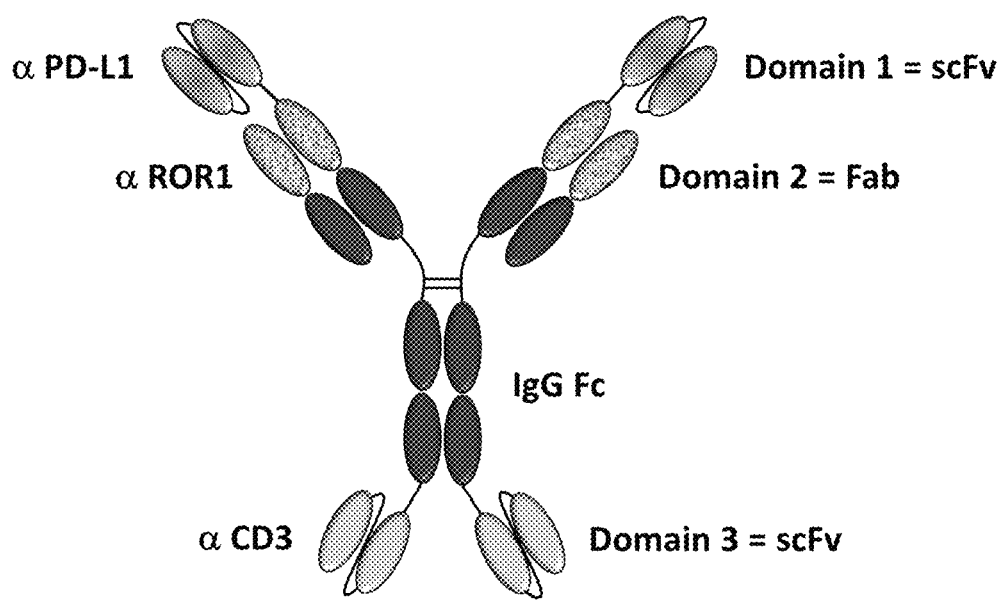

FIGURE 4 is a snapshot of experiment results showing FACS analysis of tri-specific antibodies binding to ROR1 expressing CHO cells according to some embodiments.
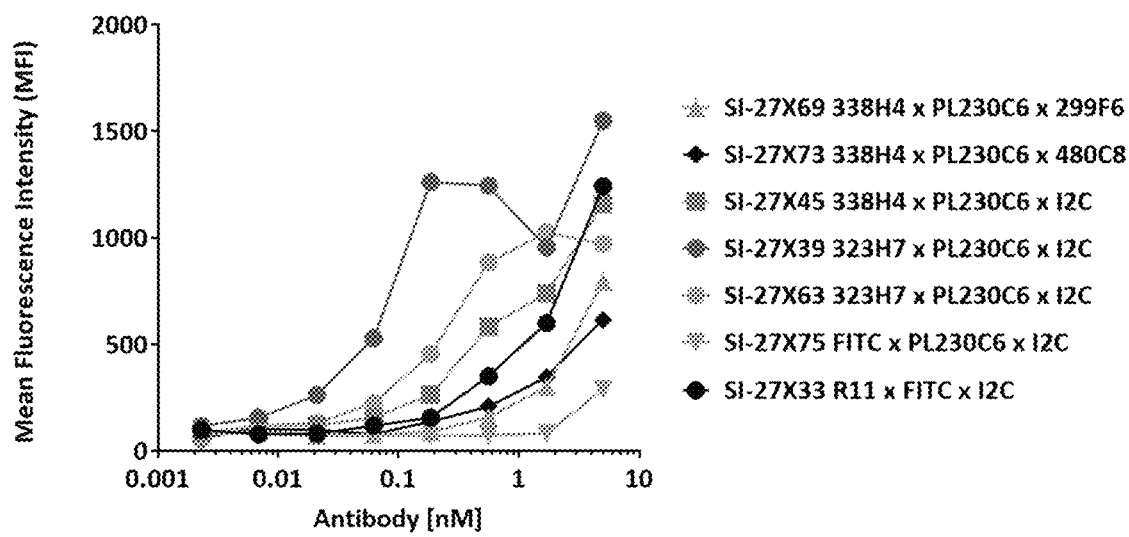
N.B: The binding domain 323H7 is specific for the Ig domain of ROR1 and the binding domain 338H4 is specific for the frizzled domain of ROR1

MULTI-SPECIFIC ANTIBODIES AND METHODS OF MAKING AND USING THEREOF
FIGURE 5 is a snapshot of experiment results showing FACS analysis of tri-specific antibody binding to PD-L1 expressing CHO cells according to some embodiments.
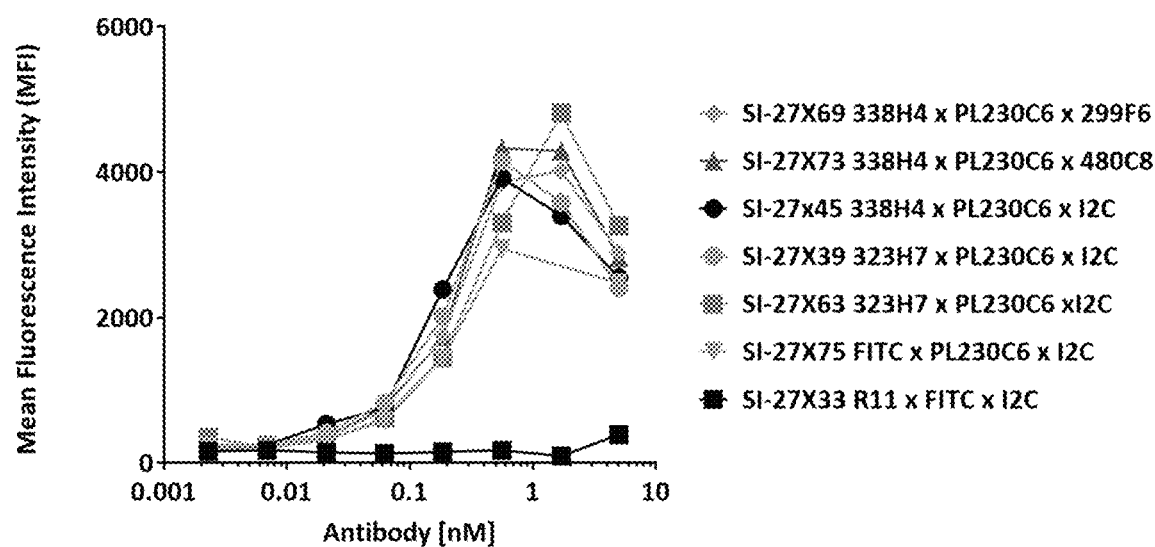

MULTI-SPECIFIC ANTIBODIES AND METHODS OF MAKING AND USING THEREOF
FIGURE 6 is a snapshot of experiment results showing re-directed T cell cytotoxicity assay with CD3+ T cells as effectors and ROR1 positive B-Acute Lymphoblastic Leukemia cell line Kasumi-2 as targets according to some embodiments.
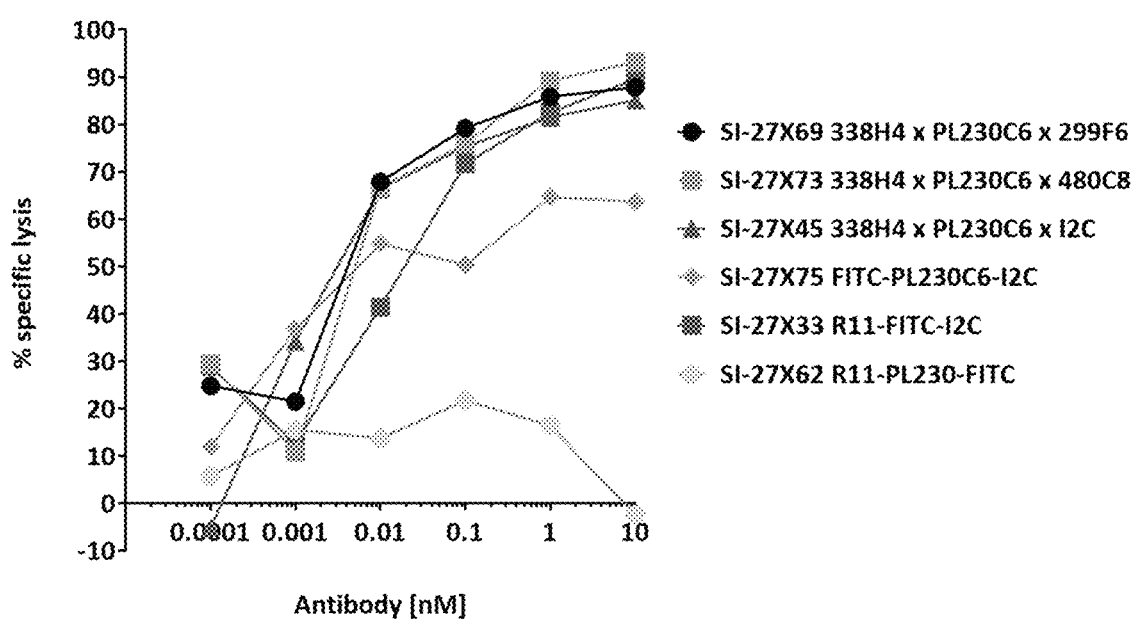

MULTI-SPECIFIC ANTIBODIES AND METHODS OF MAKING AND USING THEREOF
FIGURE 7 is a snapshot of experiment results showing re-directed T cell cytotoxicity assay with CD4+ T regulatory cells as effectors and ROR1 positive B-Acute Lymphoblastic Leukemia cell line Kasumi-2 as targets according to some embodiments.
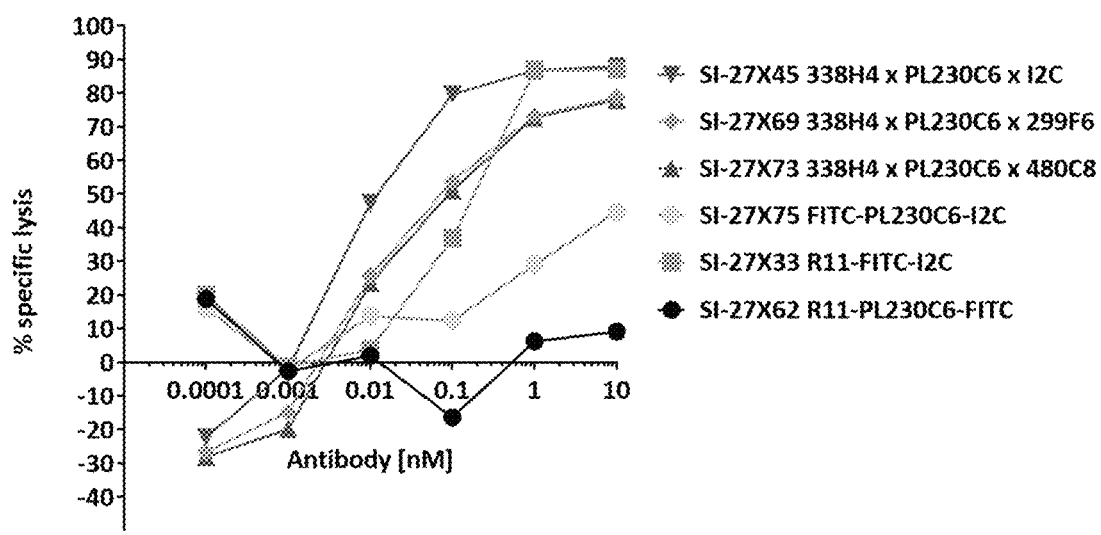

MULTI-SPECIFIC ANTIBODIES AND METHODS OF MAKING AND USING THEREOF
FIGURE 8 is a snapshot of experiment results showing re-directed T cell cytotoxicity assay with "exhausted" CD8+ T cells as effectors and ROR1 positive B-Acute Lymphoblastic Leukemia cell line Kasumi-2 as targets according to some embodiments.
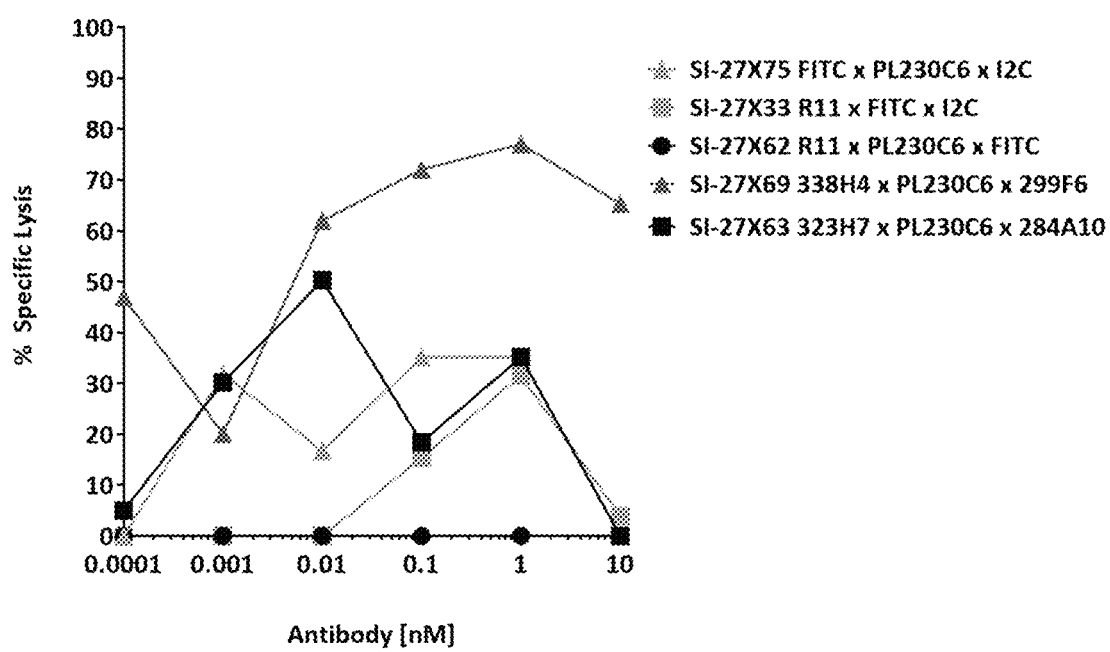

MULTI-SPECIFIC ANTIBODIES AND METHODS OF MAKING AND USING THEREOF
FIGURE 9 is a snapshot of experiment results showing re-directed T cell cytotoxicity assay with peripheral blood mononuclear cells as effectors and the glioblastoma cell line U87-EGFRviii as targets according to some embodiments.
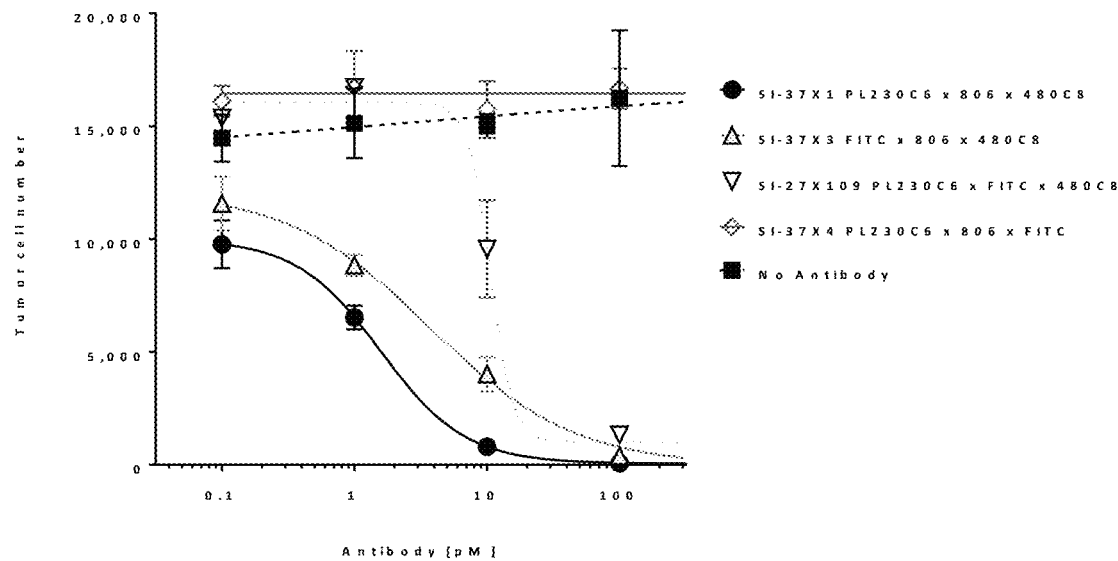

MULTI-SPECIFIC ANTIBODIES AND METHODS OF MAKING AND USING THEREOF
FIGURE 10 is a snapshot of experiment results showing re-directed T cell cytotoxicity assay with peripheral blood mononuclear cells as effectors and the glioblastoma cell line U87-EGFRviii as targets according to some embodiments.
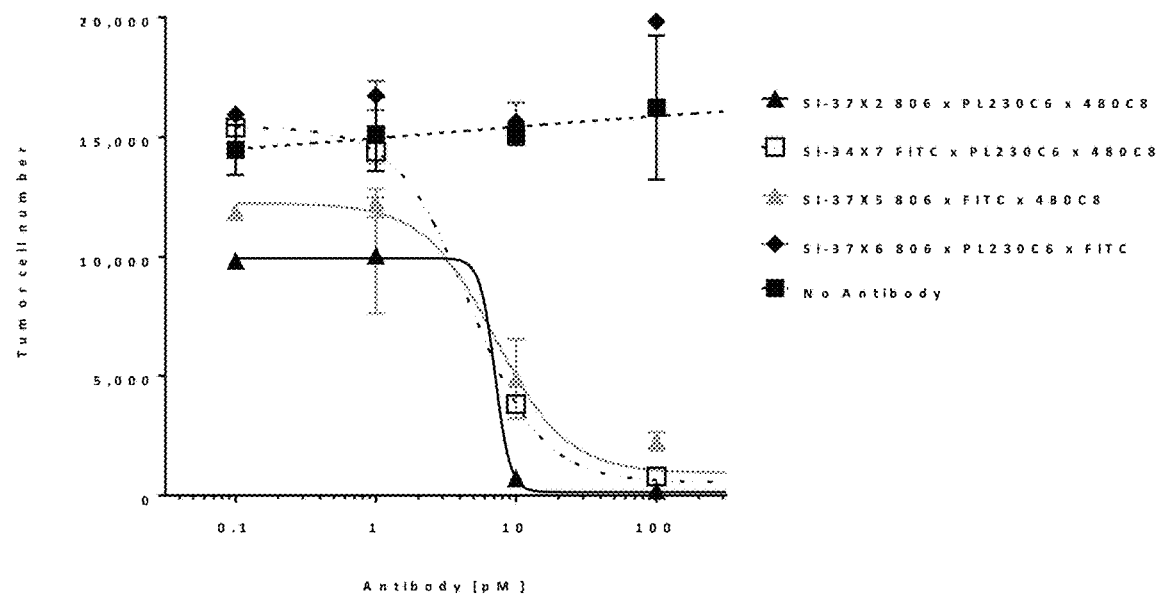

MULTI-SPECIFIC ANTIBODIES AND METHODS OF MAKING AND USING THEREOF
FIGURE 11 is a snapshot of experiment results showing re-directed T cell cytotoxicity assay with PBMC cells as effectors and CD19 positive B-Acute Lymphoblastic Leukemia cell line Kasumi-2 as targets according to some embodiments.
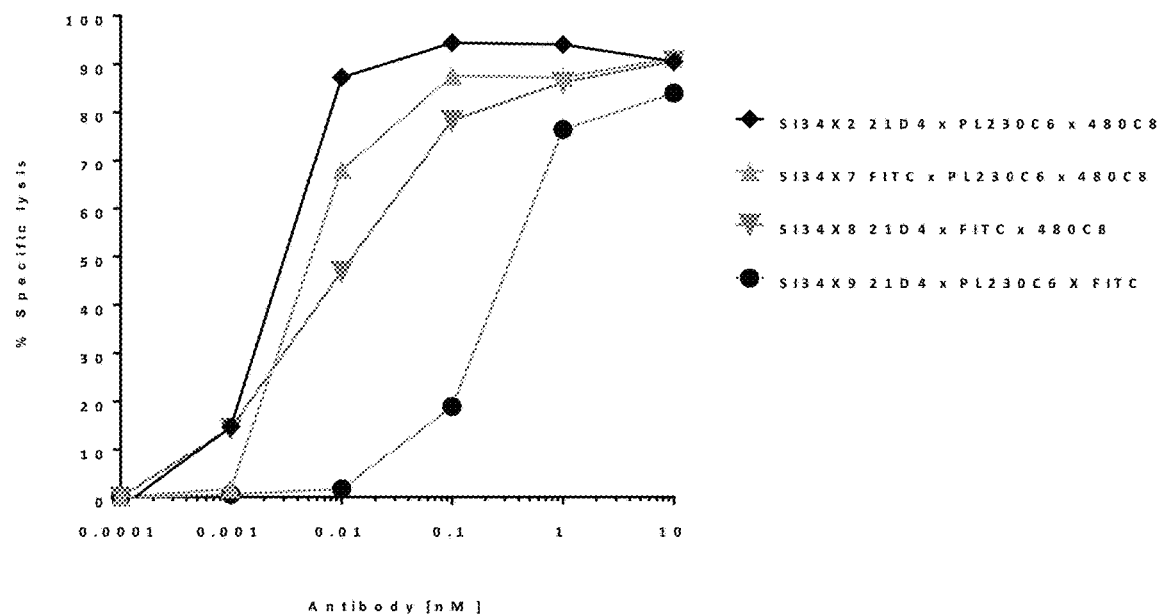

TRI-SPECIFIC ANTIBODIES

CROSS REFERENCE TO RELATED APPLICATIONS

This application claims the benefit of U.S. Provisional Patent Application No. 62/524,554, filed Jun. 25, 2017, which application is expressly incorporated herein by reference in its entirety.

TECHNICAL FIELD

The present disclosure generally relates to the technical field of biologic therapeutics, and more particularly relates to making and using multi-specific antibodies.

BACKGROUND

Cancer cells develop various strategies to evade destruction and elimination by the immune system of the host. One main mechanism is immune-editing where the immune response against the original cancer provides immunological pressure to select for variants of the original cancer cell that are not recognized by the immune system through the down-regulation of the Major Histocompatibility Complex (MHC) presentation of tumour specific antigens. Another mechanism resides within the tumour microenvironment where cells such as T regulatory cells (Treg) or Myeloid-derived suppressor cells (MDSC) actively inhibit the cytolytic activity of cytotoxic T cells or natural killer cells through the production of immune-suppressive cytokines such as Transforming Growth Factor Beta (TGFβ) or Interleukin-10 (IL-10). Also, within the tumour microenvironment cancer cells often express one or more "Immune Checkpoint" receptors or molecules such as Programmed Death Ligand 1 (PD-L1) that bind to inhibitory receptors on T cells such as Programmed cell death protein 1 (PD-1) that plays an important role in down-regulating the immune response and promoting self-tolerance. [Vinay et al., 2015, Semin. Cancer Biol., (35): S185-S198, Dunn et al., 2004, Immunity, 21(2): 137-48; Adachi & Tamada, 2015, Cancer Sci., 106(8): 945-50].

As the mechanisms by which tumours evade recognition by the immune system continue to be better understood new treatment modalities that target these mechanisms have recently emerged. On Mar. 25, 2011, the U. S. Food and Drug Administration (FDA) approved ipilimumab injection (Yervoy, Bristol-Myers Squibb) for the treatment of unresectable or metastatic melanoma. Yervoy binds to cytotoxic T-lymphocyte-associated protein 4 (CTLA-4) expressed on activated T cells and blocks the interaction of CTLA-4 with CD80/86 on antigen-presenting cells thereby blocking the negative or inhibitory signal delivered into the T cell through CTLA-4 resulting in re-activation of the antigen-specific T cell leading to, in many patients, eradication of the tumour. A few years later in 2014 the FDA approved Keytruda (Pembrolizumab, Merck) and Opdivo (Nivolumab, Bristol-Myers Squibb) for treatment of advanced melanoma. These monoclonal antibodies bind to PD-1 which is expressed on activated and/or exhausted T cells and block the interaction of PD-1 with PD-L1 expressed on tumours thereby eliminating the inhibitory signal through PD-1 into the T cell resulting in re-activation of the antigen-specific T cell leading to again, in many patients, eradication of the tumour. Since then additional clinical trials have been performed comparing the single monoclonal antibody Yervoy to the combination of the monoclonal antibodies Yervoy and Opdivo in the treatment of advanced melanoma which showed improvement in overall survival and progression-free survival in the patients treated with the combination of antibodies. (Hodi et al., 2016, Lancet Oncol. 17(11):1558-1568, Hellman et al., 2018, Cancer Cell 33(5):853-861). However, as many clinical trials have shown a great benefit of treating cancer patients with monoclonal antibodies that are specific for one or more immune checkpoint molecules data has emerged that only those patients with a high mutational burden that generates a novel T cell epitope(s) which is recognized by antigen-specific T cells show a clinical response (Snyder et al., 2014, NEJM 371:2189-2199). Those patients that have a low tumour mutational load mostly do not show an objective clinical response (Snyder et al., 2014, NEJM 371:2189-2199, Hellman et al., 2018, Cancer Cell 33(5):853-861).

In recent years other groups have developed an alternate approach that does not require the presence of neoepitope presentation by antigen-presenting cells to activate T cells. One example is the development of a bi-specific antibody where the binding domain of an antibody which is specific for a tumour associated antigen, e.g., CD19, is linked to an antibody binding domain specific for CD3 on T cells thus creating a bi-specific T cell engager or BiTe molecule. In 2014, the FDA approved a bi-specific antibody called Blinotumumab for the treatment of Precursor B-Cell Acute Lymphoblastic Leukemia. Blinotumumab links the scFv specific for CD19 expressed on leukemic cells with the scFv specific for CD3 expressed on T cells (Bejnjamin and Stein 2016, Ther Adv Hematol 7(3):142-146). However, despite an initial response rate of >50% in patients with relapsed or refractory ALL many patients are resistant to blinotumumab therapy or relapse after successful treatment with blinotumumab. Evidence is emerging that the resistance to blinotumumab or the relapse after blinotumumab treatment is attributable to the expression of immune checkpoint inhibitory molecules expressed on tumour cells such as PD-L1 that drives an inhibitory signal through PD-1 expressed on activated T cells (Feucht et al., 2016, Oncotarget 7(47): 76902-76919). In a case study of a patient who was resistant to therapy with blinotumumab a second round of blinotumumab therapy was performed but with the addition of a monoclonal antibody, pembrolizumab (Keytruda, Merck), which is specific for PD-1 and blocks the interaction of T cell-expressed PD-1 with tumour cell expressed PD-L1 resulted in a dramatic response and reduction of tumour cells in the bone marrow from 45% to less than 5% in this one patient (Feucht et al., 2016, Oncotarget 7(47):76902-76919). These results show that combining a bi-specific BiTe molecule with one or more monoclonal antibodies can significantly increase clinical activity compared to either agent alone.

SUMMARY

In one aspect, the application provides tri-specific antibody monomers, the antigen-binding fragments thereof, and multi-specific antibodies.

In one embodiment, the tri-specific antibody monomer having a N-terminal and a C-terminal, comprising in tandem from the N-terminal to the C-terminal, a first scFv domain at the N-terminal, a Fab domain, a Fc domain, and a second scFv domain at the C-terminal. The first scFv domain, the Fab domain, and the second scFv domain each has a binding specificity against a different antigen.

The antigen may be a tumour antigen, an immune signaling antigen, or a combination thereof. In one embodiment, the first scFv domain, the Fab domain, and the second scFv domain each has a binding specificity against a tumour antigen. In one embodiment, the first scFv domain, the Fab domain, and the second scFv domain each has a binding specificity against an immune signaling antigen.

In one embodiment, the first scFv domain has a binding specificity against a tumour antigen. In one embodiment, the first scFv domain has a binding specificity against an immune signaling antigen. In one embodiment, the Fab domain has a binding specificity against a tumour antigen. In one embodiment, the Fab domain has a binding specificity against an immune signaling antigen. In one embodiment, the second scFv domain has a binding specificity against a tumour antigen. In one embodiment, the second scFv domain has a binding specificity against an immune signaling antigen.

In one embodiment, the first scFv domain, the Fab domain, and the second scFv domain each independently has a binding specificity against an antigen selected from ROR1, PD-L1, CD3, CD28, 41BB, CEA, HER2, EGFRvIII, EGFR, LMP1, LMP2A, Mesothelin, PSMA, EpCAM, glypican-3, gpA33, GD2, TROP2, NKG2D, BCMA, CD19, CD20, CD33, CD123, CD22, CD30, PDL1, PD1, OX40, 4-1BB, GITR, TIGIT, TIM-3, LAG-3, CTLA4, CD40, VISTA, ICOS, BTLA, LIGHT, HVEM, CSF1R, CD73, and CD39.

In one embodiment, the first scFv domain, the Fab domain, and the second scFv domain each independently has a binding specificity against an antigen selected from ROR1, PD-L1, and CD3. In one embodiment, the first scFv domain has a binding specificity against ROR1. In one embodiment, the Fab domain has a binding specificity against PD-L1. In one embodiment, the second scFv domain has a binding specificity against CD3. In one embodiment, the first scFv domain has a binding specificity against ROR1, the Fab domain has a binding specificity against PD-L1, and the second scFv has a binding specificity against CD3.

The antibody monomers and the antibodies disclosed herein may be humanized. In one embodiment, the Fc domain is a human IgG1 Fc.

The application provides scFv domains for the tri-specific antibody monomer and antibodies disclosed herein. In one embodiment, the scFv domain includes an amino acid sequence having a percentage homology to SEQ ID NO. 13-34, 39-46. The percentage homology is not less than 70%, 80%, 90%, 95%, 98%, or 99%.

The application provides Fab domains for the tri-specific antibody monomers and antibodies disclosed herein. In one embodiment, the Fab domain includes an amino acid sequence having a percentage homology to SEQ ID NO. 13-16. The percentage homology is not less than 70%, 80%, 90%, 95%, 98%, or 99%.

The application provides Fc domains for the tri-specific antibody monomers and antibodies disclosed herein. In one embodiment, the Fab domain includes an amino acid sequence having a percentage homology to SEQ ID NO.47 and 48. The percentage homology is not less than 70%, 80%, 90%, 95%, 98%, or 99%.

The first scFv domain, the second scFv domain, the Fab domain and the Fc domain in the tri-specific antibody monomers and antibodies may be any combination of sequences disclosed herein.

In one embodiment, the application provides a multi-specific antibody, comprising a tri-specific antibody monomer. In one embodiment, the multi-specific antibody includes a first tri-specific monomer and a second tri-specific monomer. In one embodiment, the first and the second tri-specific monomers are the same and the multi-specific antibody is a symmetric tri-specific antibody. In one embodiment, the first and the second tri-specific monomers are different and the multi-specific antibody is an asymmetric antibody. In one embodiment, the multi-specific antibody is a tri-specific antibody, a tetra-specific antibody, a penta-specific antibody, or a hexa-specific antibody.

In one embodiment, the multi-specific antibody includes a first tri-specific antibody monomer and a second tri-specific antibody monomer. The first tri-specific antibody monomer has a N-terminal and a C-terminal and includes, in tandem from the N-terminal to the C-terminal, a first scFv domain at the N-terminal, a first Fab domain, a first Fc domain, and a second scFv domain at the C-terminal. The second multi-specific antibody monomer has a N-terminal and a C-terminal and includes, in tandem from the N-terminal to the C-terminal, a third scFv domain at the N-terminal, a second Fab domain, a second Fc domain, and a fourth scFv domain at the C-terminal. In one embodiment, the third scFv domain, a second Fab domain and a fourth scFv domain each has a binding specificity against a different antigen. In one embodiment, the second scFv domain and the fourth scFv domain each has a binding specificity against a different antigen. In one embodiment, the first scFv domain and the third scFv domain each has a binding specificity against a different antigen. In one embodiment, the first Fab domain and the second Fab domain each has a binding specificity against a different antigen.

In one embodiment, the multi-specific antibody is a tri-specific antibody. In one embodiment, the application provides an engineered antibody with 3 different binding domains or a "tri-specific" antibody. One binding domain is specific for CD3 on T cells, a second binding domain is specific for a tumour associated antigen including but not limited to ROR1, CEA, HER2, EGFR, EGFRvIII, LMP1, LMP2A, Mesothelin, PSMA, EpCAM, glypican-3, gpA33, GD2, TROP2, BCMA, CD19, CD20, CD33, CD123, CD22, CD30, and a third binding domain which is specific for an immune checkpoint modulator such as PDL1, PD1, OX40, 4-1BB, GITR, TIGIT, TIM-3, LAG-3, CTLA4, CD40, VISTA, ICOS, BTLA, Light, HVEM, CD73, CD39, etc. In one embodiment, the tri-specific antibody includes an amino acid sequence having a percentage homology to SEQ ID NO as disclosed in this application. The percentage homology is not less than 70%, 80%, 90%, 95%, 98%, or 99%.

In one embodiment, the antibody is purified, isolated, or non-natural existing.

The application further provides the isolated nucleic acid sequence encoding the tri-specific monomers, the antigen-binding fragments thereof, or the multi-specific antibodies disclosed herein. In one embodiment, the isolated nucleic acid sequence encodes the tri-specific antibody monomer disclosed herein.

The application further provides expression vector or host cells including the isolated nucleic acid sequence disclosed herein. In one embodiment, the host cell includes the expression vector. In one embodiment, the host cell is a prokaryotic cell or a eukaryotic cell.

The application further provides immuno-conjugates including a cytotoxic agent or an imaging agent linked to the tri-specific antibody monomers, the antigen-binding fragments, or the multi-specific antibodies through a linker.

The linker may be cleavable or non-cleavable. In one embodiment, the linker may be a covalent bond such as an ester bond, an ether bond, an amid bond, a disulphide bond, an imide bond, a sulfone bond, a phosphate bond, a phosphorus ester bond, a peptide bond, or a combination thereof. In one embodiment, the linker may include a hydrophobic poly(ethylene glycol) linker.

The cytotoxic agent may include a chemotherapeutic agent, a growth inhibitory agent, a cytotoxic agent from class of calicheamicin, an antimitotic agent, a toxin, a radioactive isotope, a therapeutic agent, or a combination thereof. In one embodiment, the cytotoxic agent may include a calicheamicin, ozogamicin, monomethyl auristatin E, emtansine, a derivative or a combination thereof.

The imaging agent may be any compound useful for imaging purpose. In one embodiment, the imaging agent may be radionuclide, a florescent agent, a quantum dots, or a combination thereof.

In another aspect, the application provides methods of making the antibody monomers, their antigen-binding fragments, or antibodies disclosed herein. In one embodiment, the method for producing a multi-specific antibody includes the steps of culturing a host cell containing the nucleic acid sequences encoding the antibodies so that the DNA sequence encoding the antibody is expressed and purifying said antibody.

In a further aspect, the application provides pharmaceutical compositions. In one embodiment, the pharmaceutical composition includes a pharmaceutically acceptable carrier and the tri-specific antibody monomers, the multi-specific antibodies, the immuno-conjugate, or a combination thereof.

In one embodiment, the pharmaceutical composition further includes a therapeutic agent. The therapeutic agent may include a radioisotope, radionuclide, a toxin, a chemotherapeutic agent, an antibody, an enzyme, or a combination thereof. In one embodiment, the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, an immune check point inhibitor, or a combination thereof.

In a further aspect, the application provides methods for treating or preventing a cancer using the tri-specific antibody monomers, the multi-specific antibodies, the immuno-conjugate, or a combination thereof. In one embodiment, the method includes administering an effective amount of the tri-specific antibody monomers, the multi-specific antibodies, the immuno-conjugate, or a combination thereof to a subject in need of such treatment. In one embodiment, the method includes administering to a subject in need of such treatment an effective amount of a pharmaceutical composition comprising the tri-specific antibody monomers, the multi-specific antibodies, the immuno-conjugate, or a combination thereof. In one embodiment, the method of treating a subject with a cancer includes administering to the subject an effective amount of the tri-specific antibody disclosed herein.

In one embodiment, the method includes directly injecting into the tumour site an effective amount of multi-specific monomers, multi-specific antibodies, the immuno-conjugates, the antigen-binding fragment thereof.

In some embodiments, the advantages that the disclosed methods of treatment have over currently existing therapies include, without limitation: 1) Inclusion of an IgG Fc domain will confer the characteristic of a longer half-life in serum compared to a bi-specific BiTe molecule, 2) Inclusion of a binding domain which is specific for an immune checkpoint modulator e.g., PD-L1, may inhibit the suppressive effect of tumour expressed PD-L1 binding to PD-1 expressed on an activated T cell, and 3) Cross-link CD3 on T cells with tumour associated antigens thus "re-directing" T cells to kill the tumour without the need to remove T cells from the patient and genetically modify them to be specific for the tumour cell before re-introducing them back into the patient as done for chimeric antigen receptor T cells (CAR-T).

Varieties of cancer may be treated with the tri-specific antibody monomers, the multi-specific antibodies, the immuno-conjugate, or a combination thereof. Example cancers include without limitation breast cancer, colorectal cancer, anal cancer, pancreatic cancer, gallbladder cancer, bile duct cancer, head and neck cancer, nasopharyngeal cancer, skin cancer, melanoma, ovarian cancer, prostate cancer, urethral cancer, lung cancer, non-small lung cell cancer, small cell lung cancer, brain tumour, glioma, neuroblastoma, esophageal cancer, gastric cancer, liver cancer, kidney cancer, bladder cancer, cervical cancer, endometrial cancer, thyroid cancer, eye cancer, sarcoma, bone cancer, leukemia, myeloma or lymphoma. In one embodiment, the cancer comprises cells expressing ROR1, CEA, HER2, EGFR, EGFRvIII, LMP1, LMP2A, Mesothelin, PSMA, EpCAM, glypican-3, gpA33, GD2, TROP2, NKG2D, BCMA, CD19, CD20, CD33, CD123, CD22, CD30.

The method of treating a subject may include co-administering an effective amount of a therapeutic agent. In one embodiment, the therapeutic agent comprises an antibody, a chemotherapy agent, an enzyme, or a combination thereof. In one embodiment, the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, or a combination thereof.

In one embodiment, the therapeutic agent comprises capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, trastuzumab, a derivative or a combination thereof.

In one embodiment, the therapeutic agent comprises a check point inhibitor. In one embodiment, the therapeutic agent comprises an inhibitor of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

The subject be treated may be a human. In one embodiment, the application provides a solution comprising an effective concentration of the tri-specific antibody monomers, the antigen-binding fragments thereof, the multi-specific antibodies, of a combination thereof, and the solution is blood plasma in a subject.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS AND TABLES

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 shows the example tri-specific antibodies used in binding and RTCC assays.

FIG. 2 shows the specificity of the antibody binding domains used in the example tri-specific antibodies.

FIG. 3 is a diagram showing a symmetric tri-specific antibody according to at least one embodiment.

FIG. 4 is a snapshot of experiment results showing FACS analysis of tri-specific antibodies binding to ROR1 expressing CHO cells according to some embodiments.

FIG. 5 is a snapshot of experiment results showing FACS analysis of tri-specific antibody binding to PD-L1 expressing CHO cells according to some embodiments.

FIG. 6 is a snapshot of experiment results showing re-directed T cell cytotoxicity assay with CD3+ T cells as effectors and ROR1 positive B-Acute Lymphoblastic Leukemia cell line Kasumi-2 as targets according to some embodiments.

FIG. 7 is a snapshot of experiment results showing re-directed T cell cytotoxicity assay with CD4+ T regulatory cells as effectors and ROR1 positive B-Acute Lymphoblastic Leukemia cell line Kasumi-2 as targets according to some embodiments.

FIG. 8 is a snapshot of experiment results showing re-directed T cell cytotoxicity assay with "exhausted" CD8+ T cells as effectors and ROR1 positive B-Acute Lymphoblastic Leukemia cell line Kasumi-2 as targets according to some embodiments.

FIG. 9 is a snapshot of experiment results showing re-directed T cell cytotoxicity assay with peripheral blood mononuclear cells as effectors and the glioblastoma cell line U87-EGFRviii as targets according to some embodiments.

FIG. 10 is a snapshot of experiment results showing re-directed T cell cytotoxicity assay with peripheral blood mononuclear cells as effectors and the glioblastoma cell line U87-EGFRviii as targets according to some embodiments.

FIG. 11 is a snapshot of experiment results showing re-directed T cell cytotoxicity assay with PBMC cells as effectors and CD19 positive B-Acute Lymphoblastic Leukemia cell line Kasumi-2 as targets according to some embodiments.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The disclosure provides, among others, isolated antibodies, methods of making such antibodies, bispecific or multi-specific molecules, antibody-drug conjugates and/or immuno-conjugates composed from such antibodies or antigen binding fragments, pharmaceutical compositions containing the antibodies, bispecific or multi-specific molecules, antibody-drug conjugates and/or immuno-conjugates, the methods for making the molecules and compositions, and the methods for treating cancer using the molecules and compositions disclosed herein.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity. In some embodiments, the antibody may be monoclonal, polyclonal, chimeric, single chain, bispecific or bi-effective, simianized, human and humanized antibodies as well as active fragments thereof. Examples of active fragments of molecules that bind to known antigens include Fab, F(ab')$_2$, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, Nature, 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with both human PD-L1 protein and cells transiently expressing human PD-L1 on the cell surface. Rabbits are known to create antibodies of high affinity, diversity and specificity (Weber et al. Exp. Mol. Med. 49:e305). B cells from immunized animals were cultured in vitro and screened for the production of anti-PD-L1 antibodies. The antibody variable genes were isolated using recombinant DNA techniques and the resulting antibodies were expressed recombinantly and further screened for desired features such as ability to inhibit the binding of PD-L1 to PD-1, the ability to bind to non-human primate PD-L1 and the ability to enhance human T-cell activation. This general method of antibody discovery is similar to that described in Seeber et al. PLOS One. 9:e86184 (2014).

The term "antigen- or epitope-binding portion or fragment" refers to fragments of an antibody that are capable of binding to an antigen (PD-L1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller sub-fragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen- or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an $F(ab')_2$ fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic a binding specificity.

"Recombinant" means the antibodies are generated using recombinant nucleic acid techniques in exogenous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

In one aspect, the application provides tri-specific antibody monomers, antigen-binding fragments thereof, and the multi-specific antibodies. In some embodiments, the application describes the generation of symmetric tri-specific antibodies and antigen-binding fragments thereof. In one embodiment, the tri-specific antibody is a dimer of a monomer having 3 different antibody binding domains.

The monomer has an N-terminal single-chain fragment variable (scFv) with one binding specificity, followed by the fragment antibody (Fab) domain with a second binding specificity, followed by a human IgG1 CH1, hinge, CH2, and CH3 domains, followed by an scFv with a third binding specificity at the C-terminal.

The corresponding kappa or lambda light chain is expressed as a separate VL-CL chain as with a typical antibody. The monomer has one domain binding to a tumour associated antigen, one domain binding to an immune checkpoint domain with either agonist or antagonist characteristics, and one domain binding to the CD3 complex on T cells, as shown in FIG. 3.

In one embodiment, N-terminal scFv are oriented VL-VH, operably linked by a 20 amino acid G4S linker and C-terminal scFv are oriented VH-VL, linked by either a 15 or 20 amino acid G4S linker. Each of these linkers genetically fuses the C-terminus of one domain to the N-terminus of its partner domain. N-terminal scFv are fused to the Fab domain with a shorter, 10 amino acid G4S linker. Likewise, the C-terminal scFv are fused to the end of the human IgG1 Fc domain with a 10 amino acid G4S linker.

In one embodiment, the symmetric tri-specific antibodies were designed to bind a tumour associated antigen (TAA) such a sROR1 (Karvonen et al, 2017, Biochem Soc Trans, 45(2): 457-464; Aghebati-Maleki et al, 2017, Biomed Pharmacother. 88:814-822; Shabani et al, 2015, Expert Opin Ther Targets. 19(7):941-55) or CD19 (Johnsen et al., 2014 Leuk Lymphoma, 55(6):1251-60) or the viii mutant of the epidermal growth factor receptor (Gan et al., 2013, FEBS J. 280(21):5350-70).

In one embodiment, the tri-specific antibodies were designed to bind to a second antigen involved in the immune response against cancer cells such as PD-L1 which is expressed on many tumours in the tumour microenvironment (Dunn & Rao, 2017, Mol Immunol. 13; 87:227-239; Balar & Weber. 2017, Cancer Immunol Immunother. 66(5): 551-564).

In one embodiment, the tri-specific antibodies were also designed to bind to a third antigen, CD3, which is T-cell specific. Antibodies of this class can bind to the tumour through the TAA and/or PD-L1 while engaging any CD3+ T-cells in the vicinity of the tumour through CD3, a process referred to as re-directed T-cell cytotoxicity or RTCC (Baeuerle and Reinhardt, 2009, Cancer res. 69(12):4941-4).

Cytotoxicity is generally achieved through the actions of CD8+ T-cells although a role for CD4+ T-cells has been demonstrated (Haas et al., 2009 Immunobiology, 214(6): 441-53). In addition, the PD-L1 binding domain used in these tri-specific antibodies has been selected to block the interaction of PD-1 on T cells with PD-L1 expressed on the tumour cells thus reducing or eliminating this inhibitory pathway to T cell activation (Feucht et al., 2016, Oncotarget 7(47):76902-76919).

To eliminate cross-linking of tri-specific antibodies on the surface of cells expressing Fc-receptors, amino acid mutations (alanine) near the IgG1 hinge region were introduced at positions L234, L235, and G237 (Strohl W R, 2009, Curr Opin Biotechnol. 20(6):685-91) resulting in an Fc domain without antibody-dependent cellular cytotoxicity (ADCC) or complement-dependent cytotoxicity (CDC) effector function referred to as an "effector null" phenotype.

In one embodiment, the tri-specific molecules target either human ROR1 (SEQIDs 5-8), human CD19 (SEQIDs 43-46) or EGFR vIII (SEQIDs 39-42) as tumour associated antigens. Each of these targeted tri-specific proteins also carries an anti-human PD-L1 (SEQIDs 13-16) and anti-human CD3 binding domain (SEQIDs 21-24). These binding domains were converted to scFv, VLVH, for placement at the N-terminal Domain 1 (D1) or scFv, VHVL, for placement at the C-terminal Domain 3 (D3) of the peptide.

In one embodiment, the scFv molecules described herein contain a 20 amino acid flexible (G4S)×4 linker that operably links the VH and VL, regardless of the V-region orientation (LH or HL). The remaining position in the tri-specific protein, Domain 2 (D2), consists of an IgG1 heavy chain, VH-CH1-Hinge-CH2-CH3, and its corresponding light chain, VL-CL, which can be either a kappa or lambda chain. D1 and D2 are genetically linked through a 10 amino acid (G4S)×2 linker, as are D2 and D3 resulting in a contiguous ~125 kDa heavy chain peptide.

When co-transfected with the appropriate light chain, the example symmetric tri-specific peptide can be subsequently purified through the IgG1 Fc (Protein A/Protein G) and assayed to assess functional activity. Heavy and light chain gene "cassettes" were previously constructed such that V-regions could be cloned using either restriction enzyme sites (HindIII/NheI for the heavy chain and HindIII/BsiWI for the light chain) or "restriction-free cloning" such as Gibson Assembly (SGI-DNA, La Jolla, Calif.), Infusion (Takara Bio USA),) or NEBuilder (NEB, Ipswich, Mass.), the latter of which was used here.

The application provides methods for making the tri-specific antibody monomers, antigen-binding fragments thereof, and the multi-specific antibodies. In one embodiment, the antibody is a tri-specific antibody. The tri-specific antibody proteins are produced through a process that involves design of the intact molecule, synthesis and cloning of the nucleotide sequences for each domain, expression in mammalian cells and purification of the final product.

Nucleotide sequences were assembled using the Geneious 10.2.3 software package (Biomatters, Auckland, NZ) and broken up into their component domains for gene synthesis (Genewiz, South Plainsfield, N.J.). In this example, SI-27X63 (SEQID 52) was split into its component domains where the anti-human ROR1 Ig domain-specific clone 338H4 VLVH scFv occupies D1, anti-human PD-L1 clone PL230C6 occupies D2 (Fab position) and anti-human CD3 clone 284A10 VHVL scFv occupies the C-terminal D3.

Using NEBuilder web-based tools, 5' and 3' nucleotides were appended to each of the domains depending on their position in the larger protein so that each domain overlaps its flanking domains by 20-30 nucleotides which direct site-specific recombination, thus genetically fusing each domain in a single gene assembly step.

A small aliquot was transformed into E. coli DH10b (Invitrogen, Carlsbad, Calif.) and plated on TB+carbenicillin 100 ug/ml plates (Teknova, Hollister, Calif.) and incubated at 37 C overnight. Resultant colonies were selected and 2 ml overnight cultures inoculated in TB+carbenicillin. DNA was prepared (Thermo-Fisher, Carlsbad, Calif.) from overnight cultures and subsequently sequenced (Genewiz, South Plainsfield, N.J.) using sequencing primers (Sigma, St. Louis, Mo.) flanking each domain. All DNA sequences were assembled and analysed in Geneious.

In another aspect, the application provides pharmaceutical compositions including the tri-specific antibody monomers, the multi-specific antibodies, the antigen-binding fragments, and the immuno-conjugates thereof. Formulation of the pharmaceutical composition can be accomplished according to standard methodology know to those of ordinary skill in the art.

In one embodiment, the antibodies and monomers according to the disclosure can be prepared in a physiologically acceptable formulation and may comprise a pharmaceutically acceptable carrier, diluent and/or excipient using known techniques. For example, the antibody as described herein may include any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Suitable pharmaceutical carriers, diluents and/or excipients are well known in the art and include, for example, phosphate buffered saline solutions, water, emulsions such as oil/water emulsions.

"Pharmaceutically acceptable" refers to those compounds, materials, compositions, and dosage forms which are, within the scope of sound medical judgment, suitable for use contact with the tissues of human beings or animals without excessive toxicity, irritation, or other problem or complication, commensurate with a reasonable benefit/risk ratio.

In one embodiment, the pharmaceutical composition may include proteinaceous carriers such as, for example, serum albumin or immunoglobulin, particularly of human origin. Further biologically active agents may be present in the pharmaceutical composition of the disclosure dependent on the intended use. In one embodiment, the proteinaceous pharmaceutically active matter may be present in amounts between 1 ng and 10 mg per dose. Generally, the regime of administration should be in the range of between 0.1 µg and 10 mg of the antibody according to the disclosure, particularly in a range 1.0 µg to 1.0 mg, and more particularly in a range of between 1.0 µg and 100 µg, with all individual numbers falling within these ranges also being part of the disclosure. If the administration occurs through continuous infusion a more proper dosage may be in the range of between 0.01 µg and 10 mg units per kilogram of body weight per hour with all individual numbers falling within these ranges also being part of the disclosure.

The compositions may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumour site, or may be implanted for systematic release of the therapeutic composition, for example, subcutaneously.

Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

It is well known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The term "therapeutically effective amount" or "effective amount" refers to the amount of antibody which, when administered to a human or animal, elicits a response which is sufficient to result in a therapeutic effect in said human or animal, e.g., to ameliorate disease in a subject. The effective amount is readily determined by one of ordinary skill in the art following routine procedures. Where the disease is a cancer, the effective amount of the drug may inhibit (for example, slow to some extent, inhibit or stop) one or more of the following example characteristics including, without limitation, cancer cell growth, cancer cell proliferation, cancer cell motility, cancer cell infiltration into peripheral organs, tumor metastasis, and tumor growth. Wherein the disease is a caner, the effective amount of the drug may alternatively do one or more of the following when administered to a subject: slow or stop tumor growth, reduce tumor size (for example, volume or mass), relieve to some extent one or more of the symptoms associated with the cancer, extend progression free survival, result in an objective response (including, for example, a partial response or a complete response), and increase overall survival time. To the extent the drug may prevent growth and/or kill existing cancer cells, it is cytostatic and/or cytotoxic.

A person skilled in the art have the ability to determine the effective amount or concentration of the antibodies disclosed therein to effective treat a condition such as a cancer. Other parameters such as the proportions of the various components in the pharmaceutical composition, administration does and frequency may be obtained by a person skilled in the art without undue experimentation. For example, a suitable solution for injection may contain, without limitation, from about 1 to about 20, from about 1 to about 10 mg antibodies per ml. The example dose may be, without limitation, from about 0.1 to about 20, from about 1 to about 5 mg/Kg body weight. The example administration frequency could be, without limitation, once per day or three times per week.

The compositions may be administered by standard routes of administration. In general, the composition may be administered by topical, oral, rectal, nasal, intradermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumour. The method includes administration of a single dose, administration of repeated doses at predetermined time intervals, and sustained administration for a predetermined period of time.

Although many forms of administration are possible, an example administration form would be a solution for injection, in particular for intravenous or intra-arterial injection. Usually, a suitable pharmaceutical composition for injection may include pharmaceutically suitable carriers or excipients such as, without limitation, a buffer, a surfactant, or a stabilizer agent. Example buffers may include, without limitation, acetate, phosphate or citrate buffer. Example surfactants may include, without limitation, polysorbate. Example stabilizer may include, without limitation, human albumin.

In one embodiment, the administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The antibody monomers, antibodies, antigen-binding fragments and immuno-conjugates thereof may be used in combination with a therapeutic agent or a composition comprising a therapeutic agent for treatment purpose. In some embodiments, the multi-specific antibody molecule is used in combination with one or more additional therapeutic agents at an effective amount. The additional therapeutic agent includes an antibody, a chemotherapy agent, an enzyme, or a combination thereof. In some embodiment, the additional therapeutic agent can be an anti-estrogen agent, a receptor tyrosine kinase inhibitor, a kinase inhibitor, a cell cycle inhibitor, a DNA, RNA or protein synthesis inhibitor, a RAS inhibitor, or a combination thereof. In some embodiments, the additional therapeutic agent can be a check point inhibitor. In some embodiments, therapeutic agent comprises inhibitors of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

In one embodiment, the therapeutic agent may capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, trastuzumab, a derivative or a combination thereof.

Cancers, including breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer, may express cancer-associated genes. Inhibition of cancer-associated activity with specific monoclonal antibodies or antigen-binding fragment may have therapeutic effect on cancers. Furthermore, administering a therapeutically effective amount of composition comprising monoclonal antibodies or antigen-binding fragment specific for cancer-associated protein may cure, prevent, ameliorate, and delay the development or metastasis of cancers, through the effect of the cytotoxic agent.

The present disclosure may be understood more readily by reference to the following detailed description of specific embodiments and examples included herein. Although the present disclosure has been described with reference to specific details of certain embodiments thereof, it is not intended that such details should be regarded as limitations upon the scope of the disclosure.

EXAMPLES

Example 1: FACS Analysis of Tri-Specific Antibody Binding to ROR1 Expressing CHO Cells The tri-specific antibodies listed in tables 1 and 2 were tested for binding to Chinese hamster ovary cells (CHO) cells stably expressing full length human ROR1. Antibodies were prepared at 2× final concentration and titrated 1:3 across 8 wells of a 96 well plate in 50 ul of PBS/2% FBS and then 5,000 ROR1-CHO cells in 50 ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA and the binding profile is shown in FIG. 4. All of the tri-specific antibodies that contained a ROR1 binding domain bound at varying levels to the CHO-ROR1 cells.

Example 2: FACS Analysis of Tri-Specific Antibody Binding to PD-L1 Expressing CHO Cells The tri-specific antibodies listed in tables 1 and 2 were tested for binding to Chinese hamster ovary cells (CHO) cells stably expressing full length human PD-L1. Antibodies were prepared at 2× final concentration and titrated 1:3 across 8 wells of a 96 well plate in 50 ul of PBS/2% FBS and then 5,000 PD-L1-CHO cells in 50 ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA and the binding profile is shown in FIG. 5. All of the tri-specific antibodies that contained a PD-L1 binding domain bound at similar levels to the CHO-PD-L1 cells.

Example 3: Re-Directed T Cell Cytotoxicity (RTCC) Assay with CD3+ T Cells as Effectors and B-Acute Lymphoblastic Leukemia (B-ALL) Cell Line Kasumi-2 as Targets The tri-specific antibodies listed in tables 1 and 2 were tested for RTCC activity against the B-ALL cell line Kasumi 2 using human CD3+ T cells as effectors. The Kasumi 2 target cells, 5×10e6, were labeled with CFSE (Invitrogen, # C34554) at 0.5 uM in 10 ml of culture media for 20 minutes at 37 C. The cells were washed 3 times with 50 ml of culture media before resuspending in 10 ml then counted again.

Antibodies were prepared at 4× final concentration and titrated 1:10 across 10 wells of a 96 well plate in 200 ul of RPMI+10% FBS. Human CD3+ T cells were enriched from peripheral blood mononuclear cells from a normal donor using the EasySep™ Human T Cell Enrichment Kit (Stemcell Technologies, #19051) as per the manufacturers protocol. The final cell population was determined to be 98% CD3+ T cells by FACS analysis (data not shown). In the final destination 96 well plate the target cells, T cells, and serially titrated antibodies were combined by adding 100 ul of target cells (5,000), 50 ul of CD3+ T cells (50,000), and 50 ul of each antibody dilution to each well of the assay. The assay plate was incubated at 37 C for approximately 72 hours and then the contents of each assay well were harvested and analyzed for the number of CFSE-labeled target cells remaining. As shown on FIG. 6, all of the tri-specific antibodies that contained a ROR1 binding domain potently killed the target cells at less than 0.01 nM or 10 pM except for the control SI-27X62 which has a FITC binding domain in the C-terminal domain 3 position which does not bind to CD3+ T cells.

Example 4: Re-Directed T Cell Cytotoxicity (RTCC) Assay with CD4+ T Regulatory Cells as Effectors and B-Acute Lymphoblastic Leukemia (B-ALL) Cell Line Kasumi-2 as Targets The tri-specific antibodies listed in tables 1 and 2 were tested for RTCC activity against the B-ALL cell line Kasumi 2 using human CD4+ T regulatory cells as effectors. The Kasumi 2 target cells, 5×10e6, were labeled with CFSE (Invitrogen, # C34554) at 0.5 uM in 10 ml of culture media for 20 minutes at 37 C. The cells were washed 3 times with 50 ml of culture media before resuspending in 10 ml then counted again. Antibodies were prepared at 4× final concentration and titrated 1:10 across 10 wells of a 96 well plate in 200 ul of RPMI+10% FBS. Human CD4+ T regulatory cells were generated using the EasySep™ Human CD4+ CD127lowCD25+ Regulatory T Cell Isolation Kit (Stemcell #18063) as per the manufacturers protocol. Enriched T regulatory cells were stimulated using Miltenyi CD3/CD28 activation beads (#-130-095-353) and cultured for 14 days in complete RPMI, supplemented with 5% human serum and 500 U/ml recombinant human IL-2 (Peprotech #200-02). The final population of T regulatory cells were analyzed by FACS to be more than 90% CD127low CD25$^{++}$ (Data not shown). In the final destination 96 well plate the target cells, T cells, and serially titrated antibodies were combined by adding 100 ul of target cells (5,000), 50 ul of CD4+ T regulatory cells (50,000), and 50 ul of each antibody dilution to each well of the assay. The assay plate was incubated at 37 C for approximately 72 hours and then the contents of each assay well were harvested and analyzed for the number of CFSE-labeled target cells remaining. As shown on FIG. 7, all of the tri-specific antibodies that contained a ROR1 binding domain potently killed the target cells at less than 0.1 nM or 100 pM except for the control SI-27X62 which has a FITC binding domain in the C-terminal domain 3 position which does not bind to CD3+ T cells.

Example 5: Re-Directed T Cell Cytotoxicity (RTCC) Assay with "Exhausted" CD8+ T Cells as Effectors and B-Acute Lymphoblastic Leukemia (B-ALL) Cell Line Kasumi-2 as Targets The tri-specific antibodies listed in tables 1 and 2 were tested for RTCC activity against the B-ALL cell line Kasumi 2 using "exhausted" human CD8+ T cells as effectors. The Kasumi 2 target cells, 5×10e6, were labeled with CFSE (Invitrogen, # C34554) at 0.5 uM in 10 ml of culture media for 20 minutes at 37 C. The cells were washed 3 times with 50 ml of culture media before resuspending in 10 ml then counted again. Antibodies were prepared at 4× final concentration and titrated 1:10 across 10 wells of a 96 well plate in 200 ul of RPMI+10% FBS. Human CD8+ T cells were enriched using the EasySep™ Human CD8+ T Cell Enrichment Kit (Stemcell #19053) as per the manufacturers protocol. Enriched CD8+ T cells were stimulated using Miltenyi CD3/CD28 activation beads (#-130-095-353) and cultured for 7 days in complete RPMI, supplemented with 5% human serum and 500 U/ml recombinant human IL-2 (Peprotech #200-02). The final population of exhausted CD8+ T cells were analyzed by FACS to be more than 95% CD8+ cells expressing several markers of exhaustion e.g., PD-1, TIGIT, TIM-3, and LAG-3 (Data not shown). In the final destination 96 well plate the target cells, T cells, and serially titrated antibodies were combined by adding 100 ul of target cells (5,000), 50 ul of exhausted CD8+ T cells (50,000), and 50 ul of each antibody dilution to each well of the assay. The assay plate was incubated at 37 C for approximately 72 hours and then the contents of each assay well were harvested and analyzed for the number of CFSE-labeled target cells remaining. As shown on FIG. 8, the tri-specific antibodies that contained the 338H4 ROR1 binding domain potently killed the target cells at less than 0.01 nM or 10 pM whereas those antibodies with the R11 or 323H7 ROR1 binding domain only weakly killed the target cells and the control SI-27X62 which has a FITC binding domain in the C-terminal domain 3 position which does not bind to CD3+ T cells showed negative killing activity.

Example 6: Re-Directed T Cell Cytotoxicity (RTCC) Assay with Peripheral Blood Mononuclear Cells as Effectors and the U87 Human Glioblastoma Cell Line Transfected with the Epidermal Growth Factor viii (EGFRviii) Mutant as Targets The tri-specific antibodies listed in tables 1 and 2 were tested for RTCC activity against the U87-EGFRviii cell line using human PBMC as effectors. The U87-EGFR viii was transduced with the NucLight Red Lentivirus (IncuCyte®) to generate a cell line that stably expresses the fluorescent mKate2 protein (Shcherbo et al., 2009, J. Biochem, 418(3): 567-574). Antibodies were prepared at 4× final concentration and titrated 1:10 across 3 wells of a 96 well plate in 200 ul of RPMI+10% FBS. Human PBMC were purified by standard ficoll density gradient from a "leukopak" which is an enriched leukapheresis product collected from normal human peripheral blood. In the final destination 96 well plate the target cells, PBMC, and serially titrated antibodies were combined by adding 100 ul of target cells (5,000), 50 ul of PBMC (200,000), and 50 ul of each antibody dilution to each well of the assay. The assay plate was incubated at 37 C for approximately 72 hours and then the contents of each assay well were harvested and analyzed for the number of NucLight Red target cells remaining. As shown in FIG. 9, the set of tri-specific molecules with the configuration of PL230×806×480C8 directed potent killing of target cells at 10 pM or more antibody. The control antibody, SI-37X3 FITC×806×480C8 which does not contain the PD-L1 binding domain PL230C6 also potently killed target cells but with slightly lower potency that the tri-specific antibody with the PD-L1 binding domain, SI-37X1 PL230C6×806×480C8. The control tri-specific antibody SI-27X109 PL230C6×FITC×480C8 which does not contain the EGFRviii binding domain 806 showed much weaker killing of target cells and the control tri-specific antibody SI-37X4 PL230C6×806×FITC that does not contain the CD3 binding domain 480C8 showed negligible killing of target cells. As shown in FIG. 10, the set of tri-specific molecules with the configuration of 806×PL230C6×480C8 directed potent killing of target cells at 10 pM or more antibody with the tri-specific antibody SI-37X2 806×PL230C6×480C8 being more potent than the 3 control tri-specific antibodies with a FITC binding domain in each of the 3 positions of the tri-specific.

Example 7: Re-Directed T Cell Cytotoxicity Assay with PBMC Cells as Effectors and CD19 Positive B-Acute Lymphoblastic Leukemia Cell Line Kasumi-2 as Targets The tri-specific antibodies listed in tables 1 and 2 were tested for RTCC activity against the B-ALL cell line Kasumi 2 using PBMC as effectors. The Kasumi 2 target cells, 5×10e6, were labeled with CFSE (Invitrogen, # C34554) at 0.5 uM in 10 ml of culture media for 20 minutes at 37 C. The cells were washed 3 times with 50 ml of culture media before resuspending in 10 ml then counted again. Antibodies were prepared at 4× final concentration and titrated 1:10 across 10 wells of a 96 well plate in 200 ul of RPMI+10% FBS. Human PBMC were purified by standard ficoll density gradient from a "leukopak" which is an enriched leukapheresis product collected from normal human peripheral blood. In the final destination 96 well plate the target cells, T cells, and serially titrated antibodies were combined by adding 100 ul of target cells (5,000), 50 ul of PBMC (50,000), and 50 ul of each antibody dilution to each well of the assay. The assay plate was incubated at 37 C for approximately 72 hours and then the contents of each assay well were harvested and analyzed for the number of CFSE-labeled target cells remaining. As shown on FIG. 10, the tri-specific antibody SI34X2 21D4×PL230C6×480C8 potently killed the target cells at less than 0.01 nM compared to the 3 control tri-specific antibodies with a FITC binding domain in each of the 3 positions of the tri-specific.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description. All references cited or referred to in this disclosure are hereby incorporated by reference in their entireties.

```
SEQUENCE LISTING
The antibody complementary Determining Regions (CDR) are defined using the
KABAT numbering system and are underlined in the amino acid (aa) sequence listing:
Light Chain
CDR1: residues 24-34
CDR2: residues 50-56
CDR3: residues 89-97

Heavy Chain
CDR1: residues 31-35
CDR2: residues 50-65
CDR3: residues 95-102 anti-ROR1 R11 VH nt
                                                                    >SEQ ID NO: 1
CAGTCCGTGAAGGAGTCCGAGGGCGACCTGGTGACCCCCGCCGGCAACCTGACCCTGACCTGCACCGCCTCCGGC

TCCGACATCAACGACTACCCCATCTCCTGGGTGCGGCAGGCCCCCGGCAAGGGCCTGGAGTGGATCGGCTTCATC

AACTCCGGCGGCTCCACCTGGTACGCCTCCTGGGTGAAGGGCCGGTTCACCATCTCCCGGACCTCCACCACCGTG

GACCTGAAGATGACCTCCCTGACCACCGACGACACCGCCACCTACTTCTGCGCCCGGGGCTACTCCACCTACTAC

GGCGACTTCAACATCTGGGGCCCCGGCACCCTGGTGACCATCTCCTCG anti-ROR1 R11 VH aa
                                                                    >SEQ ID NO: 2
QSVKESEGDLVTPAGNLTLTCTASGSDIN DYPIS WVRQAPGKGLEWIG FINSGGSTWYASWVKG RFTISRTSTTV

DLKMTSLTTDDTATYFCAR GYSTYYGDFNI WGPGTLVTISS anti-ROR1 R11 VL nt
                                                                    >SEQ ID NO: 3
GAGCTGGTGATGACCCAGACCCCCTCCTCCACCTCCGGCGCCGTGGGCGGCACCGTGACCATCAACTGCCAGGCC

TCCCAGTCCATCGACTCCAACCTGGCCTGGTTCCAGCAGAAGCCCGGCCAGCCCCCCACCCTGCTGATCTACCGG

GCCTCCAACCTGGCCTCCGGCGTGCCCTCCCGGTTCTCCGGCTCCCGGTCCGGCACCGAGTACACCCTGACCATC

TCCGGCGTGCAGCGGGAGGACGCCGCCACCTACTACTGCCTGGGCGGCGTGGGCAACGTGTCCTACCGGACCTCC

TTCGGCGGCGGCACCGAGGTGGTGGTGAAG anti-ROR1 R11 VL aa
                                                                    >SEQ ID NO: 4
ELVMTQTPSSTSGAVGGTVTINC QASQSIDSNLA WFQQKPGQPPTLLIY RASNLAS GVPSRFSGSRSGTEYTLTI

SGVQREDAATYYC LGGVGNVSYRTS FGGGTEVVVK anti-ROR1 323H7 VHv4 nt
                                                                    >SEQ ID NO: 5
GAGGTGCAGCTGTTGGAGTCTGGGGGAGGCTTGGTACAGCCTGGGGGGTCCCTGAGACTCTCCTGTGCAGCCTCT

GGATTCACCATCAGTCGCTACCACATGACTTGGGTCCGCCAGGCTCCAGGGAAGGGGCTGGAGTGGATCGGACAT

ATTTATGTTAATAATGATGACACAGACTACGCGAGCTCCGCGAAAGGCCGGTTCACCATCTCCAGAGACAATTCC

AAGAACACGCTGTATCTGCAAATGAACAGCCTGAGAGCCGAGGACACGGCCACCTATTTCTGTGCGAGATTGGAT

GTTGGTGGTGGTGGTGCTTATATTGGGGACATCTGGGGCCAGGGAACTCTGGTTACCGTCTCTTCA anti-ROR1 323H7 VHv4 aa
                                                                    >SEQ ID NO: 6
EVQLLESGGGLVQPGGSLRLSCAAS GFTISRYHMT WVRQAPGKGLEWIG HIYVNNDDTDYASSAKG RFTISRDNS

KNTLYLQMNSLRAEDTATYFCAR LDVGGGGAYIGDI WGQGTLVTVSS anti-ROR1 323H7 VLv1 nt
                                                                    >SEQ ID NO: 7
GACATCCAGATGACCCAGTCTCCATCCTCCCTGTCTGCATCTGTAGGAGACAGAGTCACCATCACTTGCCAGTCC

AGTCAGAGTGTTTATAACAACAACGACTTAGCCTGGTATCAGCAGAAACCAGGGAAAGTTCCTAAGCTCCTGATC

TATTATGCTTCCACTCTGGCATCTGGGGTCCCATCTCGGTTCAGTGGCAGTGGATCTGGGACAGATTTCACTCTC

ACCATCAGCAGCCTGCAGCCTGAAGATGTTGCAACTTATTACTGTGCAGGCGGTTATGATACGGATGGTCTTGAT

ACGTTTGCTTTCGGCGGAGGGACCAAGGTGGAGATCAAA
```

-continued anti-ROR1 323H7 VLv1 aa
>SEQ ID NO: 8
DIQMTQSPSSLSASVGDRVTITCQSSQSVYNNNDLAWYQQKPGKVPKLLIYYASTLASGVPSRFSGSGSGTDFTL

TISSLQPEDVATYYCAGGYDTDGLDTFAFGGGTKVEIK anti-ROR1 338H4 VHv3 nt
>SEQ ID NO: 9
GAGGTGCAGCTGGTGGAGTCTGGGGGAGGCTTGGTCCAGCCTGGGGGGTCCCTGAGACTCTCCTGTACTGCCTCT

GGATTCTCCCTCAGTAGCTATGCAATGAGCTGGGTCCGCCAGGCTCCAGGGAGGGGGCTGGAGTGGATCGGAATC

ATTTATGCTAGTGGTAGCACATACTACGCGAGCTCGGCGAAAGGCAGATTCACCATCTCCAAAGACAATACCAAG

AACACGGTGGATCTTCAAATGAACAGCCTGAGAGCCGAGGACACGGCTGTGTATTACTGTGCGAGAATTTATGAC

GGCATGGACCTCTGGGGCCAGGGAACTCTGGTTACCGTCTCTTCA anti-ROR1 338H4 VHv3 aa
>SEQ ID NO: 10
EVQLVESGGGLVQPGGSLRLSCTASGFSLSSYAMSWVRQAPGRGLEWIGIIYASGSTYYASSAKGRFTISKDNTK

NTVDLQMNSLRAEDTAVYYCARIYDGMDLWGQGTLVTVSS anti-ROR1 338H4 VLv4 nt
>SEQ ID NO: 11
GACATCCAGATGACCCAGTCTCCATCCTCCCTGTCTGCATCTGTAGGAGACAGAGTCACCATCAATTGCCAGGCC

AGTCAGAACATTTACAGCTACTTATCCTGGTATCAGCAGAAACCAGGGAAAGTTCCTAAGCGCCTGATCTATCTG

GCATCTACTCTGGCATCTGGGGTCCCATCTCGGTTCAGTGGCAGTGGATCTGGGACAGATTACACTCTCACCATC

AGCAGCCTGCAGCCTGAAGATGTTGCAACTTATTACTGTCAAAGCAATTATAACGGTAATTATGGTTTCGGCGGA

GGGACCAAGGTGGAGATCAAA anti-ROR1 338H4 VLv4 aa
>SEQ ID NO: 12
DIQMTQSPSSLSASVGDRVTINCQASQNIYSYLSWYQQKPGKVPKRLIYLASTLASGVPSRFSGSGSGTDYTLTI

SSLQPEDVATYYCQSNYNGNYGFGGGTKVEIK anti-PD-L1 PL230C6 VHv3 nt
>SEQ ID: 13
CAGTCGGTGGAGGAGTCTGGGGGAGGCTTGGTCCAGCCTGGGGGGTCCCTGAGACTCTCCTGTACAGCCTCTGGA

ATCGACCTTAATACCTACGACATGATCTGGGTCCGCCAGGCTCCAGGCAAGGGGCTAGAGTGGGTTGGAATCATT

ACTTATAGTGGTAGTAGATACTACGCGAACTGGGCGAAAGGCCGATTCACCATCTCCAAAGACAATACCAAGAAC

ACGGTGTATCTGCAAATGAACAGCCTGAGAGCTGAGGACACGGCTGTGTATTACTGTGCCAGAGATTATATGAGT

GGTTCCCACTTGTGGGGCCAGGGAACCCTGGTCACCGTCTCTAGT anti-PD-L1 PL230C6 VHv3 aa
>SEQ ID: 14
QSVEESGGGLVQPGGSLRLSCTASGIDLNTYDMIWVRQAPGKGLEWVGIITYSGSRYYANWAKGRFTISKDNTKN

TVYLQMNSLRAEDTAVYYCARDYMSGSHLWGQGTLVTVSS anti-PD-L1 PL230C6 VLv2 nt
>SEQ ID: 15
GCCTATGATATGACCCAGTCTCCATCTTCCGTGTCTGCATCTGTAGGAGACAGAGTCACCATCAAGTGTCAGGCC

AGTGAGGACATTTATAGCTTCTTGGCCTGGTATCAGCAGAAACCAGGGAAAGCCCCTAAGCTCCTGATCCATTCT

GCATCCTCTCTGGCATCTGGGGTCCCATCAAGGTTCAGCGGCAGTGGATCTGGGACAGATTTCACTCTCACCATC

AGCAGCCTGCAGCCTGAAGATTTTGCAACTTACTATTGTCAACAGGGTTATGGTAAAAATAATGTTGATAATGCT

TTCGGCGGAGGGACCAAGGTGGAGATCAAA anti-PD-L1 PL230C6 VLv2 aa
>SEQ ID: 16
AYDMTQSPSSVSASVGDRVTIKCQASEDIYSFLAWYQQKPGKAPKLLIHSASSLASGVPSRFSGSGSGTDFTLTI

SSLQPEDFATYYCQQGYGKNNVDNAFGGGTKVEIK anti-CD3 I2C VH nt
>SEQ ID: 17
CAGGTGCAATTGGTGGAAAGCGGAGGGGGACTGGTGCAGCCCGGGGGAAGTCTGAAGCTGTCCTGTGCCGCCAGC

GGCTTTACCTTCAACAAGTACGCCATGAATTGGGTCCGACAGGCCCCAGGGAAAGGCCTGGAATGGGTGGCACGG

ATTCGGTCCAAGTACAACAACTACGCCACCTACTACGCTGACTCCGTGAAGGACAGATTCACCATCAGCCGGGAC

GACTCTAAGAACACCGCCTATCTGCAGATGAACAACCTGAAAACCGAGGATACAGCTGTGTACTATTGTGTGCGG

CACGGCAACTTCGGCAACTCCTACATCTCCTACTGGGCCTATTGGGGACAGGGAACACTGGTCACCGTGTCTAGC anti-CD3 I2C VH aa
>SEQ ID: 18
QVQLVESGGGLVQPGGSLKLSCAASGFTFNKYAMNWVRQAPGKGLEWVARIRSKYNNYATYYADSVKDRFTISRD

DSKNTAYLQMNNLKTEDTAVYYCVRHGNFGNSYISYWAYWGQGTLVTVSS anti-CD3 I2C VL nt
>SEQ ID: 19
CAGACCGTGGTCACCCAGGAACCTTCCCTGACCGTCTCCCCAGGCGGCACCGTGACCCTGACCTGTGGCTCCTCT

ACCGGCGCTGTGACCTCCGGCAACTACCCTAACTGGGTGCAGCAGAAACCCGGACAGGCTCCTAGAGGCCTGATC

GGCGGCACCAAGTTTCTGGCCCCTGGCACCCCTGCCAGATTCTCCGGCTCCCTGCTGGGAGGCAAGGCCGCTCTG

ACCCTGTCTGGCGTGCAGCCTGAGGACGAGGCCGAGTACTACTGTGTGCTGTGGTACTCCAACAGATGGGTGTTC

GGAGGCGGCACAAAGCTGACCGTGCTGTCCTCG anti-CD3 I2C VL aa
>SEQ ID: 20
QTVVTQEPSLTVSPGGTVTLTCGSSTGAVTSGNYPNWVQQKPGQAPRGLIGGTKFLAPGTPARFSGSLLGGKAAL

TLSGVQPEDEAEYYCVLWYSNRWVFGGGTKLTVLSS anti-CD3 284A10 VHv1 nt
>SEQ ID: 21
GAGGTGCAGCTGGTGGAGTCTGGGGGAGGCTTGGTCCAGCCTGGGGGGTCCCTGAGACTCTCCTGTGCAGCCTCT

GGATTCACCATCAGTACCAATGCAATGAGCTGGGTCCGCCAGGCTCCAGGGAAGGGGCTGGAGTGGATCGGAGTC

ATTACTGGTCGTGATATCACATACTACGCGAGCTGGGCGAAAGGCAGATTCACCATCTCCAGAGACAATTCCAAG

AACACGCTGTATCTTCAAATGAACAGCCTGAGAGCCGAGGACACGGCTGTGTATTACTGTGCGCGCGACGGTGGA

TCATCTGCTATTACTAGTAACAACATTTGGGGCCAAGGAACTCTGGTCACCGTTTCTTCA anti-CD3 284A10 VHv1 aa
>SEQ ID: 22
EVQLVESGGGLVQPGGSLRLSCAASGFTISTNAMSWVRQAPGKGLEWIGVITGRDITYYASWAKGRFTISRDNSK

NTLYLQMNSLRAEDTAVYYCARDGGSSAITSNNIWGQGTLVTVSS anti-CD3 284A10 VLv1 nt
>SEQ ID: 23
GACGTCGTGATGACCCAGTCTCCTTCCACCCTGTCTGCATCTGTAGGAGACAGAGTCACCATCAATTGCCAAGCC

AGTGAGAGCATTAGCAGTTGGTTAGCCTGGTATCAGCAGAAACCAGGGAAAGCCCCTAAGCTCCTGATCTATGAA

GCATCCAAACTGGCATCTGGGGTCCCATCAAGGTTCAGCGGCAGTGGATCTGGGACAGAGTTCACTCTCACCATC

AGCAGCCTGCAGCCTGATGATTTTGCAACTTATTACTGCCAAGGCTATTTTTATTTTATTAGTCGTACTTATGTA

AATTCTTTCGGCGGAGGGACCAAGGTGGAGATCAAA anti-CD3 284A10 VLv1 aa
>SEQ ID: 24
DVVMTQSPSTLSASVGDRVTINCQASESISSWLAWYQQKPGKAPKLLIYEASKLASGVPSRFSGSGSGTEFTLTI

SSLQPDDFATYYCQGYFYFISRTYVNSFGGGTKVEIK anti-CD3 299F6 VHv2 nt
>SEQ ID: 25
GAGGTGCAGCTGGTGGAGTCTGGGGGAGGCTTGGTCCAGCCTGGGGGGTCCCTGAGACTCTCCTGTACGGCCTCT

GGATTCACCATCAGTAGCAATGCAATGAGCTGGGTCCGCCAGGCTCCAGGGAAGGGGCTGGAGTGGATCGGAGTC

ATTACTGGTCGTGATATCACATACTACGCGAGCTGGGCGAAAGGCAGATTCACCATCTCCAAAGACACCTCCAAG

```
AACACGGTGGATCTTCAAATGAACAGCCTGAGAGCCGAGGACACGGCTGTGTATTACTGTGCGCGCGACGGTGGA

TCATCTGCTATTACTAGTAACAACATTTGGGGCCAAGGAACTCTGGTCACCGTTTCTTCA
``` anti-CD3 299F6 VHv2 aa
                                                                     >SEQ ID: 26
EVQLVESGGGLVQPGGSLRLSCTASGFTIS<u>SNAMS</u>WVRQAPGKGLEWIG<u>VITGRDITYYASWAKG</u>RFTISKDTSK NTVDLQMNSLRAEDTAVYYCAR<u>DGGSSAITSNN</u>IWGQGTLVTVSS anti-CD3 299F6 VLv1 nt
                                                                     >SEQ ID: 27
```
GACATCCAGATGACCCAGTCTCCTTCCACCCTGTCTGCATCTGTAGGAGACAGAGTCACCATCACTTGCCAAGCC

AGTGAGAGCATTAGCAGTTGGTTAGCCTGGTATCAGCAGAAACCAGGGAAAGCCCCTAAGCTCCTGATCTATGAA

GCATCCAAACTGGCATCTGGGGTCCCATCAAGGTTCAGCGGCAGTGGATCTGGGACAGAGTTCACTCTCACCATC

AGCAGCCTGCAGCCTGATGATTTTGCAACTTATTACTGCCAAGGCTATTTTTATTTTATTAGTCGTAGTTATGTA

AATGCTTTCGGCGGAGGGACCAAGGTGGAGATCAAA
``` anti-CD3 299F6 VLv1 aa
                                                                     >SEQ ID: 28
DIQMTQSPSTLSASVGDRVTITC<u>QASESISSWLA</u>WYQQKPGKAPKLLIY<u>EASKLAS</u>GVPSRFSGSGSGTEFTLTI SSLQPDDFATYYC<u>QGYFYFISRSYVNA</u>FGGGTKVEIK anti-CD3 480C8 VHv1 nt
                                                                     >SEQ ID: 29
```
GAGGTGCAGCTGGTGGAGTCTGGGGGAGGCTTGGTCCAGCCTGGGGGGTCCCTGAGACTCTCCTGTGCAGCCTCT

GGAATCGACCTCAGTAGCAATGCAATGAGCTGGGTCCGCCAGGCTCCAGGGAAGGGGCTGGAGTGGATCGGAGTC

ATTACTGGTCGTGATATCACATACTACGCGAGCTGGGCGAAAGGCAGATTCACCATCTCCAGAGACAATTCCAAG

AACACGCTGTATCTTCAAATGAACAGCCTGAGAGCCGAGGACACGGCTGTGTATTACTGTGCGCGCGACGGTGGA

TCATCTGCTATTAATAGTAAGAACATTTGGGGCCAAGGAACTCTGGTCACCGTTTCTTCA
``` anti-CD3 480C8 VHv1 aa
                                                                     >SEQ ID: 30
EVQLVESGGGLVQPGGSLRLSCAASGIDLS<u>SNAMS</u>WVRQAPGKGLEWIG<u>VITGRDITYYASWAKG</u>RFTISRDNSK NTLYLQMNSLRAEDTAVYYCAR<u>DGGSSAINSKNI</u>WGQGTLVTVSS anti-CD3 480C8 VHv2 nt
                                                                     >SEQ ID: 31
```
GAGGTGCAGCTGGTGGAGTCTGGGGGAGGCTTGGTCCAGCCTGGAGGGTCCCTGAGACTCTCCTGTACGGCCTCT

GGAATCGACCTCAGTAGCAATGCAATGAGCTGGGTCCGCCAGGCTCCAGGGAAAGGGCTGGAGTGGATCGGAGTC

ATTACTGGTCGTGATATCACATACTACGCGAGCTGGGCGAAAGGCAGATTCACCATCTCCAAAGACACCTCCAAG

AACACGGTGGATCTTCAAATGAACAGCCTGAGAGCCGAGGACACGGCTGTGTATTACTGTGCGCGCGACGGTGGA

TCATCTGCTATTAATAGTAAGAACATTTGGGGCCAAGGAACTCTGGTCACCGTTTCTTCA
``` anti-CD3 480C8 VHv2 aa
                                                                     >SEQ ID: 32
EVQLVESGGGLVQPGGSLRLSCTASGIDLS<u>SNAMS</u>WVRQAPGKGLEWIG<u>VITGRDITYYASWAKG</u>RFTISKDTSK NTVDLQMNSLRAEDTAVYYCAR<u>DGGSSAINSKNI</u>WGQGTLVTVSS anti-CD3 480C8 VLv1 nt
                                                                     >SEQ ID: 33
```
GACATCCAGATGACCCAGTCTCCTTCCACCCTGTCTGCATCTGTAGGAGACAGAGTCACCATCACTTGCCAAGCC

AGTGAGAGCATTAGCAGTTGGTTAGCCTGGTATCAGCAGAAACCAGGGAAAGCCCCTAAGCTCCTGATCTATGAA

GCATCCAAACTGGCATCTGGGGTCCCATCAAGGTTCAGCGGCAGTGGATCTGGGACAGAGTTCACTCTCACCATC

AGCAGCCTGCAGCCTGATGATTTTGCAACTTATTACTGCCAAGGCTATTTTTATTTTATTAGTCGTACTTATGTA

AATGCTTTCGGCGGAGGGACCAAGGTGGAGATCAAA
``` anti-CD3 480C8 VLv1 aa
>SEQ ID: 34
DIQMTQSPSTLSASVGDRVTITCQASESISSWLAWYQQKPGKAPKLLIYEASKLASGVPSRFSGSGSGTEFTLTI
SSLQPDDFATYYCQGYFYFISRTYVNAFGGGTKVEIK anti-FITC 4-4-2-(4420) VH nt
>SEQ ID: 35
GAGGTGAAGCTGGATGAGACTGGAGGAGGCTTGGTGCAACCTGGGAGGCCCATGAAACTCTCCTGTGTTGCCTCT
GGATTCACTTTTAGTGACTACTGGATGAACTGGGTCCGCCAGTCTCCAGAGAAAGGACTGGAGTGGGTAGCACAA
ATTAGAAACAAACCTTATAATTATGAAACATATTATTCAGATTCTGTGAAAGGCAGATTCACCATCTCAAGAGAT
GATTCCAAAAGTAGTGTCTACCTGCAAATGAACAACTTAAGAGTTGAAGACATGGGTATCTATTACTGTACGGGT
TCTTACTATGGTATGGACTACTGGGGTCAAGGAACCTCAGTCACCGTCTCCTCA anti-FITC 4-4-2-(4420) VH aa
>SEQ ID: 36
EVKLDETGGGLVQPGRPMKLSCVASGFTFSDYWMNWVRQSPEKGLEWVAQIRNKPYNYETYYSDSVKGRFTISRD
DSKSSVYLQMNNLRVEDMGIYYCTGSYYGMDYWGQGTSVTVSS anti-FITC 4-4-2-(4420) VL nt
>SEQ ID: 37
GATGTCGTGATGACCCAAACTCCACTCTCCCTGCCTGTCAGTCTTGGAGATCAAGCCTCCATCTCTTGCAGATCT
AGTCAGAGCCTTGTACACAGTAATGGAAACACCTATTTACGTTGGTACCTGCAGAAGCCAGGCCAGTCTCCAAAG
GTCCTGATCTACAAAGTTTCCAACCGATTTTCTGGGGTCCCAGACAGGTTCAGTGGCAGTGGATCAGGGACAGAT
TTCACACTCAAGATCAGCAGAGTGGAGGCTGAGGATCTGGGAGTTTATTTCTGCTCTCAAAGTACACATGTTCCG
TGGACGTTCGGTGGAGGCACCAAGCTGGAAATCAAA anti-FITC 4-4-2-(4420) VL aa
>SEQ ID: 38
DVVMTQTPLSLPVSLGDQASISCRSSQSLVHSNGNTYLRWYLQKPGQSPKVLIYKVSNRFSGVPDRFSGSGSGTD
FTLKISRVEAEDLGVYFCSQSTHVPWTFGGGTKLEIK anti-EGFRvIII mAb 806 VH nt
>SEQ ID: 39
GATGTGCAGCTTCAGGAGTCGGGACCTAGCCTGGTGAAACCTTCTCAGTCTCTGTCCCTCACCTGCACTGTCACT
GGCTACTCAATCACCAGTGATTTTGCCTGGAACTGGATTCGGCAGTTTCCAGGAAACAAGCTGGAGTGGATGGGC
TACATAAGTTATAGTGGTAACACTAGGTACAACCCATCTCTCAAAAGTCGAATCTCTATCACTCGCGACACATCC
AAGAACCAATTCTTCCTGCAGTTGAACTCTGTGACTATTGAGGACACAGCCACATATTACTGTGTAACGGCGGGA
CGCGGGTTTCCTTATTGGGGCCAAGGGACTCTGGTCACTGTCTCTGCA anti-EGFRvIII mAb 806 VH aa
>SEQ ID: 40
DVQLQESGPSLVKPSQSLSLTCTVTGYSITSDFAWNWIRQFPGNKLEWMGYISYSGNTRYNPSLKSRISITRDTS
KNQFFLQLNSVTIEDTATYYCVTAGRGFPYWGQGTLVTVSA anti-EGFRvIII mAb 806 VL nt
>SEQ ID: 41
GACATCCTGATGACCCAATCTCCATCCTCCATGTCTGTATCTCTGGGAGACACAGTCAGCATCACTTGCCATTCA
AGTCAGGACATTAACAGTAATATAGGGTGGTTGCAGCAGAGACCAGGGAAATCATTTAAGGGCCTGATCTATCAT
GGAACCAACTTGGACGATGAAGTTCCATCAAGGTTCAGTGGCAGTGGATCTGGAGCCGATTATTCTCTCACCATC
AGCAGCCTGGAATCTGAAGATTTTGCAGACTATTACTGTGTACAGTATGCTCAGTTTCCGTGGACGTTCGGTGGA
GGCACCAAGCTGGAAATCAAA anti-EGFRvIII mAb 806 VL aa
>SEQ ID: 42
DILMTQSPSSMSVSLGDTVSITCHSSQDINSNIGWLQQRPGKSFKGLIYHGTNLDDEVPSRFSGSGSGADYSLTI
SSLESEDFADYYCVQYAQFPWTFGGGTKLEIK -continued anti-CD19 21D4 VH nt
>SEQ ID: 43
GAGGTGCAGCTGGTGCAGTCTGGAGCAGAGGTGAAGAAACCAGGAGAGTCTCTGAAGATCTCCTGTAAGGGTTCT
GGATACAGCTTTAGCAGTTCATGGATCGGCTGGGTGCGCCAGGCACCTGGGAAAGGCCTGGAATGGATGGGGATC
ATCTATCCTGATGACTCTGATACCAGATACAGTCCATCCTTCCAAGGCCAGGTCACCATCTCAGCCGACAAGTCC
ATCAGGACTGCCTACCTGCAGTGGAGTAGCCTGAAGGCCTCGGACACCGCTATGTATTACTGTGCGAGACATGTT
ACTATGATTTGGGGAGTTATTATTGACTTCTGGGGCCAGGGAACCCTGGTCACCGTCTCCTCA anti-CD19 21D4 VH aa
>SEQ ID: 44
EVQLVQSGAEVKKPGESLKISCKGSGYSFS<u>SSWIG</u>WVRQAPGKGLEWMG<u>IIYPDDSDTRYSPSFQG</u>QVTISADKS
IRTAYLQWSSLKASDTAMYYCAR<u>HVTMIWGVIIDF</u>WGQGTLVTVSS anti-CD19 21D4 VL nt
>SEQ ID: 45
GCCATCCAGTTGACCCAGTCTCCATCCTCCCTGTCTGCATCTGTAGGAGACAGAGTCACCATCACTTGCCGGGCA
AGTCAGGGCATTAGCAGTGCTTTAGCCTGGTATCAGCAGAAACCAGGGAAAGCTCCTAAGCTCCTGATCTATGAT
GCCTCCAGTTTGGAAAGTGGGGTCCCATCAAGGTTCAGCGGCAGTGGATCTGGGACAGATTTCACTCTCACCATC
AGCAGCCTGCAGCCTGAAGATTTTGCAACTTATTACTGTCAACAGTTTAATAGTTACCCATTCACTTTCGGCCCT
GGGACCAAAGTGGATATCAAA anti-CD19 21D4 VL aa
>SEQ ID: 46
AIQLTQSPSSLSASVGDRVTITC<u>RASQGISSALA</u>WYQQKPGKAPKLLIY<u>DASSLES</u>GVPSRFSGSGSGTDFTLTI
SSLQPEDFATYYC<u>QQFNSYPFT</u>FGPGTKVDIK human IgG1 null (G1m-fa with ADCC/CDC null mutations) nt
>SEQ ID: 47
GCTAGCACCAAGGGCCCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGACCGTGCCCTCCAGCAGC
TTGGGCACCCAGACCTACATCTGCAACGTGAATCACAAGCCCAGCAACACCAAGGTGGACAAGAGAGTTGAGCCC
AAATCTTGTGACAAAACTCACACATGCCCACCGTGCCCAGCACCTGAAGCCGCGGGGGCACCGTCAGTCTTCCTC
TTCCCCCCAAAACCCAAGGACACCCTCATGATCTCCCGGACCCCTGAGGTCACATGCGTGGTGGTGGACGTGAGC
CACGAAGACCCTGAGGTCAAGTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCAGGACTGGCTGAATGGCAAG
GAGTACAAGTGCGCGGTCTCCAACAAAGCCCTCCCAGCCCCCATCGAGAAAACCATCTCCAAAGCCAAAGGGCAG
CCCCGAGAACCACAGGTGTACACCCTGCCCCCATCCCGGGATGAGCTGACCAAGAACCAGGTCAGCCTGACCTGC
CTGGTCAAAGGCTTCTATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTATAGCAAGCTCACCGTGGACAAGAGCAGGTGG
CAGCAGGGGAACGTCTTCTCATGCTCCGTGATGCATGAGGCTCTGCACAACCACTACACGCAGAAGAGCCTCTCC
CTGTCTCCGGGT human IgG1 null (G1m-fa with ADCC/CDC null mutations) aa
>SEQ ID: 48
ASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKRVEPKSCDKTHTCPPCPAPEAAGAPSVFLFPPKPKDTLMISRTPEVTCVVVDVS
HEDPEVKFNWYVDGVEVHNAKTKPREEQYNSTYRVVSVLTVLHQDWLNGKEYKCAVSNKALPAPIEKTISKAKGQ
PREPQVYTLPPSRDELTKNQVSLTCLVKGFYPSDIAVEWESNGQPENNYKTTPPVLDSDGSFFLYSKLTVDKSRW
QQGNVFSCSVMHEALHNHYTQKSLSLSPG human Ig Kappa nt
>SEQ ID: 49

CGTACGGTGGCTGCACCATCTGTCTTCATCTTCCCGCCATCTGATGAGCAGTTGAAATCTGGAACTGCCTCTGTT

GTGTGCCTGCTGAATAACTTCTATCCCAGAGAGGCCAAAGTACAGTGGAAGGTGGATAACGCCCTCCAATCGGGT

AACTCCCAGGAGAGTGTCACAGAGCAGGACAGCAAGGACAGCACCTACAGCCTCAGCAGCACCCTGACGCTGAGC

AAAGCAGACTACGAGAAACACAAAGTCTACGCCTGCGAAGTCACCCATCAGGGCCTGAGCTCGCCCGTCACAAAG

AGCTTCAACAGGGGAGAGTGT human Ig Kappa aa
>SEQ ID: 50

RTVAAPSVFIFPPSDEQLKSGTASVVCLLNNFYPREAKVQWKVDNALQSGNSQESVTEQDSKDSTYSLSSTLTLS

KADYEKHKVYACEVTHQGLSSPVTKSFNRGEC

SI-27X63 (323H7-L1H4-scFv x PL230C6-H3-Fab x 284A10-H1L1-scFv) heavy chain nt
>SEQ ID: 51

GACATCCAGATGACCCAGTCTCCATCCTCCCTGTCTGCATCTGTAGGAGACAGAGTCACCATCACTTGCCAGTCC

AGTCAGAGTGTTTATAACAACAACGACTTAGCCTGGTATCAGCAGAAACCAGGGAAAGTTCCTAAGCTCCTGATC

TATTATGCTTCCACTCTGGCATCTGGGGTCCCATCTCGGTTCAGTGGCAGTGGATCTGGGACAGATTTCACTCTC

ACCATCAGCAGCCTGCAGCCTGAAGATGTTGCAACTTATTACTGTCAGGCGGTTATGATACGGATGGTCTTGAT

ACGTTTGCTTTCGGCGGAGGGACCAAGGTGGAGATCAAAGGCGGTGGCGGTAGTGGGGGAGGCGGTTCTGGCGGC

GGAGGGTCCGGCGGTGGAGGATCAGAGGTGCAGCTGTTGGAGTCTGGGGGAGGCTTGGTACAGCCTGGGGGGTCC

CTGAGACTCTCCTGTGCAGCCTCTGGATTCACCATCAGTCGCTACCACATGACTTGGGTCCGCCAGGCTCCAGGG

AAGGGGCTGGAGTGGATCGGACATATTTATGTTAATAATGATGACACAGACTACGCGAGCTCCGCGAAAGGCCGG

TTCACCATCTCCAGAGACAATTCCAAGAACACGCTGTATCTGCAAATGAACAGCCTGAGAGCCGAGGACACGGCC

ACCTATTTCTGTGCGAGATTGGATGTTGGTGGTGGTGGTGCTTATATTGGGGACATCTGGGGCCAGGGAACTCTG

GTTACCGTCTCTTCAGGCGGTGGAGGGTCCGGCGGTGGTGGATCCCAGTCGGTGGAGGAGTCTGGGGGAGGCTTG

GTCCAGCCTGGGGGGTCCCTGAGACTCTCCTGTACAGCCTCTGGAATCGACCTTAATACCTACGACATGATCTGG

GTCCGCCAGGCTCCAGGCAAGGGGCTAGAGTGGGTTGGAATCATTACTTATAGTGGTAGTAGATACTACGCGAAC

TGGGCGAAAGGCCGATTCACCATCTCCAAAGACAATACCAAGAACACGGTGTATCTGCAAATGAACAGCCTGAGA

GCTGAGGACACGGCTGTGTATTACTGTGCCAGAGATTATATGAGTGGTTCCCACTTGTGGGGCCAGGGAACCCTG

GTCACCGTCTCTAGTGCTAGCACCAAGGGCCCATCGGTCTTCCCCCTGGCACCCTCCTCCAAGAGCACCTCTGGG

GGCACAGCGGCCCTGGGCTGCCTGGTCAAGGACTACTTCCCCGAACCGGTGACGGTGTCGTGGAACTCAGGCGCC

CTGACCAGCGGCGTGCACACCTTCCCGGCTGTCCTACAGTCCTCAGGACTCTACTCCCTCAGCAGCGTGGTGACC

GTGCCCTCCAGCAGCTTGGGCACCCAGACCTACATCTGCAACGTGAATCACAAGCCCAGCAACACCAAGGTGGAC

AAGAGAGTTGAGCCCAAATCTTGTGACAAAACTCACACATGCCCACCGTGCCCAGCACCTGAAGCCGCGGGGGCA

CCGTCAGTCTTCCTCTTCCCCCCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGACGGCGTGGAGGTGCATAATGCC

AAGACAAAGCCGCGGGAGGAGCAGTACAACAGCACGTACCGTGTGGTCAGCGTCCTCACCGTCCTGCACCAGGAC

CTGGTGAATGGCAAGGAGTACAAGTGCGCGGTCTCCAACAAAGCCCTCCCAGCCCCCATCGAGAAAACCATCTCC

AAAGCCAAAGGGCAGCCCCGAGAACCACAGGTGTATACCCTGCCCCCATCCCGGGATGAGCTGACCAAGAACCAG

GTCAGCCTGACCTGCCTGGTCAAAGGCTTCTATCCCAGCGACATCGCCGTGGAGTGGGAGAGCAATGGGCAGCCG

GAGAACAACTACAAGACCACGCCTCCCGTGCTGGACTCCGACGGCTCCTTCTTCCTCTATAGCAAGCTCACCGTG

GACAAGAGCAGGTGGCAGCAGGGGAACGTCTTCTCATGCTCCGTGATGCATGAGGCTCTGCACAACCACTACACG

CAGAAGAGCCTCTCCCTGTCTCCGGGTGGCGGTGAGGGTCCGGCGGTGGTGGATCCGAGGTGCAGCTGGTGGAG

TCTGGGGGAGGCTTGGTCCAGCCTGGGGGGTCCCTGAGACTCTCCTGTGCAGCCTCTGGATTCACCATCAGTACC

-continued

AATGCAATGAGCTGGGTCCGCCAGGCTCCAGGGAAGGGGCTGGAGTGGATCGGAGTCATTACTGGTCGTGATATC

ACATACTACGCGAGCTGGGCGAAAGGCAGATTCACCATCTCCAGAGACAATTCCAAGAACACGCTGTATCTTCAA

ATGAACAGCCTGAGAGCCGAGGACACGGCTGTGTATTACTGTGCGCGCGACGGTGGATCATCTGCTATTACTAGT

AACAACATTTGGGGCCAAGGAACTCTGGTCACCGTTTCTTCAGGCGGTGGCGGTAGTGGGGGAGGCGGTTCTGGC

GGCGGAGGGTCCGGCGGTGGAGGATCAGACGTCGTGATGACCCAGTCTCCTTCCACCCTGTCTGCATCTGTAGGA

GACAGAGTCACCATCAATTGCCAAGCCAGTGAGAGCATTAGCAGTTGGTTAGCCTGGTATCAGCAGAAACCAGGG

AAAGCCCCTAAGCTCCTGATCTATGAAGCATCCAAACTGGCATCTGGGGTCCCATCAAGGTTCAGCGGCAGTGGA

TCTGGGACAGAGTTCACTCTCACCATCAGCAGCCTGCAGCCTGATGATTTTGCAACTTATTACTGCCAAGGCTAT

TTTTATTTTATTAGTCGTACTTATGTAAATTCTTTCGGCGGAGGGACCAAGGTGGAGATCAAA

SI-27X63 (323H7-L1H4-scFv x PL230C6-H3-Fab x 284A10-H1L1-scFv) heavy chain aa
>SEQ ID: 52

DIQMTQSPSSLSASVGDRVTITC<u>QSSQSVYNNNDLA</u>WYQQKPGKVPKLLIY<u>YASTLAS</u>GVPSRFSGSGSGTDFTL

TISSLQPEDVATYYC<u>AGGYDTDGLDTFA</u>FGGGTKVEIK (anti-ROR1 323H7 VLv1)

GGGGSGGGGSGGGGSGGGGS (Gly<sub>4</sub>Ser)x4 linker

EVQLLESGGGLVQPGGSLRLSCAASGFTIS<u>RYHMT</u>WVRQAPGKGLEWIG<u>HIYVNNDDTDYASSAKG</u>RFTISRDNS

KNTLYLQMNSLRAEDTATYFCAR<u>LDVGGGGAYIGDI</u>WGQGTLVTVSS (anti-ROR1 323H7 VHv4)

GGGGSGGGGS (Gly<sub>4</sub>Ser)x2 linker

QSVEESGGGLVQPGGSLRLSCTASGIDLN<u>TYDMI</u>WVRQAPGKGLEWVG<u>IITYSGSRYYANWAKG</u>RFTISKDNTKN

TVYLQMNSLRAEDTAVYYCAR<u>DYMSGSHL</u>WGQGTLVTVSS (anti-PD-L1 PL230C6 VHv3)

ASTKGPSVFPLAPSSKSTSGGTAALGCLVKDYFPEPVTVSWNSGALTSGVHTFPAVLQSSGLYSLSSVVTVPSSS

LGTQTYICNVNHKPSNTKVDKRVEPKSCDKTHTCPPCPAPEAAGAPSVFLFPPKPKDTLMISRTPEVTCVVVDVS

HEDPEVKFNWYVDGVEVHNAKTKPREEQYNSTYRVVSVLTVLHQDWLNGKEYKCAVSNKALPAPIEKTISKAKGQ

PREPQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPG (human IgG1 null)

GGGGSGGGGS (Gly<sub>4</sub>Ser)x2 linker

EVQLVESGGGLVQPGGSLRLSCAASGFTIS<u>TNAMS</u>WVRQAPGKGLEWIG<u>VITGRDITYYASWAKG</u>RFTISRDNSK

NTLYLQMNSLRAEDTAVYYCAR<u>DGSSAITSNNI</u>WGQGTLVTVSS (anti-CD3 284A10 VHv1)

GGGGSGGGGSGGGGSGGGGS (Gly<sub>4</sub>Ser)x4 linker

DVVMTQSPSTLSASVGDRVTINC<u>QASESISSWLA</u>WYQQKPGKAPKLLIY<u>EASKLAS</u>GVPSRFSGSGSGTEFTLTI

SSLQPDDFATYYC<u>QGYFYFISRTYVNS</u>FGGGTKVEIK (anti-CD3 284A10 VLv1)

SI-27X63 (323H7-L1H4-scFv x PL230C6-H3-Fab x 284A10-H1L1-scFv) light chain nt
>SEQ ID: 53

GCCTATGATATGACCCAGTCTCCATCTTCCGTGTCTGCATCTGTAGGAGACAGAGTCACCATCAAGTGTCAGGCC

AGTGAGGACATTTATAGCTTCTTGGCCTGGTATCAGCAGAAACCAGGGAAAGCCCCTAAGCTCCTGATCCATTCT

GCATCCTCTCTGGCATCTGGGGTCCCATCAAGGTTCAGCGGCAGTGGATCTGGGACAGATTTCACTCTCACCATC

AGCAGCCTGCAGCCTGAAGATTTTGCAACTTACTATTGTCAACAGGGTTATGGTAAAAATAATGTTGATAATGCT

TTCGGCGGAGGGACCAAGGTGGAGATCAAACGTACGGTGGCTGCACCATCTGTCTTCATCTTCCCGCCATCTGAT

GAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCACC

TACAGCCTCAGCAGCACCCTGACGCTGAGCAAAGCAGACTACGAGAAACACAAAGTCTACGCCTGCGAAGTCACC

CATCAGGGCCTGAGCTCGCCCGTCACAAAGAGCTTCAACAGGGGAGAGTGT

-continued

SI-27X63 (323H7-L1H4-scFv x PL230C6-H3-Fab x 284A10-H1L1-scFv) light chain aa
>SEQ ID: 54

AYDMTQSPSSVSASVGDRVTIKCQASEDIYSFLAWYQQKPGKAPKLLIHSASSLASGVPSRFSGSGSGTDFTLTI

SSLQPEDFATYYCQQGYGKNNVDNAFGGGTKVEIK (anti-PD-L1 PL230C6 VLv2)

RTVAAPSVFIFPPSDEQLKSGTASVVCLLNNFYPREAKVQWKVDNALQSGNSQESVTEQDSKDSTYSLSSTLTLS

KADYEKHKVYACEVTHQGLSSPVTKSFNRGEC (human Ig Kappa)

What is claimed is:

1. A tri-specific antibody monomer having a N-terminal and a C-terminal, comprising in tandem from the N-terminal to the C-terminal,
   a first scFv domain at the N-terminal, having a binding specificity against ROR1, PD-L1, EGFRvIII, or CD19, comprising the following pairs of sequences:
   SEQ ID NOs: (2 and 4), or (6 and 8), or (10 and 12), having the binding specific against ROR1, or
   SEQ ID NOs: (14 and 16), having the binding specific against PD-L1, or
   SEQ ID NOs: (40 and 42), having the binding specific against EGFRvIII, or
   SEQ ID NOs: (44 and 46), having the binding specific against CD 19,
   a Fab domain having a binding specificity against PD-L1, EGFRvIII, or CD19 and comprising the respective pair of sequences SEQ ID NOs: (14 and 16), or SEQ ID NOs: (40 and 42), or SEQ ID NOs: (44 and 46),
   a Fc domain, and
   a second scFv domain at the C-terminal, having a binding specificity against CD3, comprising one the following pairs of sequences SEQ ID NOs: (18 and 20), (22 and 24), (26 and 28), (30 and 32), (30 and 34),
   wherein the first scFv domain, the Fab domain, and the second scFv domain each has a binding specificity against a different antigen.

2. The tri-specific antibody monomer of claim 1, wherein the tri-specific antibody monomer comprises an amino acid sequence having 100% identity to,
   3 complementarity determining regions (CDRs) of SEQ ID NO: 6 and 3 CDRs of SEQ ID NO: 8,
   3 CDRs of SEQ ID NO: 14 and 3 CDRs of SEQ ID NO: 16,
   3 CDRs of SEQ ID NO: 22 and 3 CDRs of SEQ ID NO: 24,
   3 CDRs of SEQ ID NO: 40 and 3 CDRs of SEQ ID NO: 42, or
   3 CDRs of SEQ ID NO: 44 and 3 CDRs of SEQ ID NO: 46.

3. The tri-specific antibody monomer of claim 1, wherein the first scFv domain has a binding specificity against ROR1, wherein the Fab domain has a binding specificity against PD-L1, and wherein the second scFv has a binding specificity against CD3.

4. The tri-specific antibody monomer of claim 1, comprising a human IgG1 Fc or a human Ig Kappa light chain.

5. The tri-specific antibody monomer of claim 1, having a binding specificity to human PD-L1, human CD3, and one of human ROR1, human CD19 or EGFR VIII.

6. The tri-specific antibody monomer of claim 1, wherein the first scFv domain comprises a (G4S)$_n$ linker, wherein n is an integral from 2 to 4 and wherein the first scFv domain is linked to the Fab domain through the linker.

7. The tri-specific antibody monomer of claim 1, wherein the first scFv domain has an amino acid sequence with a binding specificity to human ROR1, wherein the amino acid sequence comprises the amino acid sequences of SEQ ID NO: 6 and SEQ ID NO: 8.

8. The tri-specific antibody monomer of claim 1, wherein the first scFv domain has an amino acid sequence with a binding specificity to human CD19, wherein the amino acid sequence comprises the amino acid sequences of SEQ ID NO: 44 and SEQ ID NO: 46.

9. The tri-specific antibody monomer of claim 1, wherein the first scFv domain has an amino acid sequence with a binding specificity to EGFR vIII, wherein the amino acid sequence comprises the amino acid sequences of SEQ ID NO: 40 and SEQ ID NO: 42.

10. The tri-specific antibody monomer of claim 1, wherein the first scFv domain has an amino acid sequence with a binding specificity to human PD-L1, wherein the amino acid sequence comprises the amino acid sequences of SEQ ID NO: 14 and SEQ ID NO: 16.

11. The tri-specific antibody-monomer of claim 1, wherein the second scFv domain has an amino acid sequence with a binding specificity to human CD3, wherein the amino acid sequence comprises the amino acid sequences of SEQ ID NO: 22 and SEQ ID NO: 24.

12. The scFv domains of the tri-specific antibody monomer of claim 1, comprising one set of pairs of amino acid sequences selected from SEQ ID NOs: (14 and 16), (40 and 42), or (44 and 46), and further comprising one set of pairs of amino acid sequences selected from SEQ ID NOs: (18 and 20), (22 and 24), (26 and 28), (30 and 32), or (30 and 34).

13. The Fab domain of the tri-specific antibody monomer of claim 1, comprising an amino acid sequence of SEQ ID NO: 14 and 16.

14. The Fc domain of the tri-specific antibody monomer of claim 1, comprising an amino acid sequence of SEQ ID NO: 48.

15. A tri-specific antibody, comprising a tri-specific antibody monomer of claim 1, wherein the tri-specific antibody has a binding specific to human PD-L1, human CD3, or one of human ROR1, human CD19 or EGFR VIII.

16. A pharmaceutical composition, comprising a pharmaceutically acceptable carrier and at least one of the multi-specific antibody of claim 15.

17. A tri-specific antibody monomer having a N-terminal and a C-terminal, comprising in tandem from the N-terminal to the C-terminal,
   a first scFv domain at the N-terminal,
   a Fab domain,
   a Fc domain, and
   a second scFv domain at the C-terminal, comprising 3 CDRs of SEQ ID NO: 22 and 3 CDRs of SEQ ID NO: 24,
   wherein the tri-specific antibody monomer comprises an amino acid sequence of 3 complementarity determining regions (CDRs) of SEQ ID NO: 14 and 3 CDRs of SEQ ID NO: 16, and one of:
   3 CDRs of SEQ ID NO: 6 and 3 CDRs of SEQ ID NO: 8,
   3 CDRs of SEQ ID NO: 40 and 3 CDRs of SEQ ID NO: 42, and
   3 CDRs of SEQ ID NO: 44 and 3 CDRs of SEQ ID NO: 46.

* * * * *

SEQUENCE LISTING

<160> NUMBER OF SEQ ID NOS: 54

<210> SEQ ID NO 1
<211> LENGTH: 348
<212> TYPE: DNA
<213> ORGANISM: Artificial Sequence
<220> FEATURE:
<223> OTHER INFORMATION: synthesized

<400> SEQUENCE: 1
cagtccgtga aggagtccga gggcgacctg gtgaccccg ccggcaacct gaccctgacc      60
tgcaccgcct ccggctccga catcaacgac taccccatct cctgggtgcg gcaggccccc     120
ggcaagggcc tggagtggat cggcttcatc aactccggcg ctccacctg gtacgcctcc      180 tgggtgaagg gccggttcac catctcccgg acctccacca ccgtggacct gaagatgacc     240
tccctgacca ccgacgacac cgccacctac ttctgcgccc ggggctactc cacctactac     300
ggcgacttca acatctgggg ccccggcacc ctggtgacca tctcctcg                  348

<210> SEQ ID NO 2
<211> LENGTH: 116
<212> TYPE: PRT
<213> ORGANISM: Artificial Sequence
<220> FEATURE:
<223> OTHER INFORMATION: synthesized

<400> SEQUENCE: 2

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Val Asp Leu Lys Met Thr
65                  70                  75                  80

Ser Leu Thr Thr Asp Asp Thr Ala Thr Tyr Phe Cys Ala Arg Gly Tyr
                85                  90                  95

Ser Thr Tyr Tyr Gly Asp Phe Asn Ile Trp Gly Pro Gly Thr Leu Val
            100                 105                 110

Thr Ile Ser Ser
        115

<210> SEQ ID NO 3
<211> LENGTH: 330
<212> TYPE: DNA
<213> ORGANISM: Artificial Sequence
<220> FEATURE:
<223> OTHER INFORMATION: synthesized

<400> SEQUENCE: 3

```
gagctggtga tgacccagac cccctcctcc acctccggcg ccgtgggcgg caccgtgacc      60
atcaactgcc aggcctccca gtccatcgac tccaacctgg cctggttcca gcagaagccc     120
ggccagcccc ccaccctgct gatctaccgg gcctccaacc tggcctccgg cgtgccctcc     180
cggttctccg gctcccggtc cggcaccgag tacaccctga ccatctccgg cgtgcagcgg     240
gaggacgccg ccacctacta ctgcctgggc ggcgtgggca acgtgtccta ccggaccctcc    300 ttcggcggcg gcaccgaggt ggtggtgaag                                      330
```

<210> SEQ ID NO 4
<211> LENGTH: 110
<212> TYPE: PRT
<213> ORGANISM: Artificial Sequence
<220> FEATURE:
<223> OTHER INFORMATION: synthesized

<400> SEQUENCE: 4

```
Glu Leu Val Met Thr Gln Thr Pro Ser Ser Thr Ser Gly Ala Val Gly
  1               5                  10                  15

Gly Thr Val Thr Ile Asn Cys Gln Ala Ser Gln Ser Ile Asp Ser Asn
             20                  25                  30

Leu Ala Trp Phe Gln Gln Lys Pro Gly Gln Pro Pro Thr Leu Leu Ile
         35                  40                  45

Tyr Arg Ala Ser Asn Leu Ala Ser Gly Val Pro Ser Arg Phe Ser Gly
     50                  55                  60

Ser Arg Ser Gly Thr Glu Tyr Thr Leu Thr Ile Ser Gly Val Gln Arg
 65                  70                  75                  80

Glu Asp Ala Ala Thr Tyr Tyr Cys Leu Gly Gly Val Gly Asn Val Ser
                 85                  90                  95

Tyr Arg Thr Ser Phe Gly Gly Gly Thr Glu Val Val Val Lys
            100                 105                 110
```

<210> SEQ ID NO 5
<211> LENGTH: 366
<212> TYPE: DNA
<213> ORGANISM: Artificial Sequence
<220> FEATURE:
<223> OTHER INFORMATION: synthesized

<400> SEQUENCE: 5

```
gaggtgcagc tgttggagtc tgggggaggc ttggtacagc ctggggggtc cctgagactc      60
tcctgtgcag cctctggatt caccatcagt cgctaccaca tgacttgggt ccgccaggct     120
ccagggaagg ggctggagtg gatcggacat atttatgtta ataatgatga cacagactac     180
gcgagctccg cgaaaggccg gttcaccatc tccagagaca attccaagaa cacgctgtat     240
ctgcaaatga acagcctgag agccgaggac acggccacct atttctgtgc gagattggat     300
gttggtggtg gtggtgctta tattgggac atctgggcc agggaactct ggttaccgtc      360
tcttca                                                                366
```

<210> SEQ ID NO 6
<211> LENGTH: 122
<212> TYPE: PRT
<213> ORGANISM: Artificial Sequence
<220> FEATURE:
<223> OTHER INFORMATION: synthesized

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Arg Tyr
            20                  25                  30

His Met Thr Trp Val Arg Gln Ala Pro Gly Lys Gly Leu Glu Trp Ile
        35                  40                  45

Gly His Ile Tyr Val Asn Asn Asp Asp Thr Asp Tyr Ala Ser Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Phe Cys
                85                  90                  95

Ala Arg Leu Asp Val Gly Gly Gly Ala Tyr Ile Gly Asp Ile Trp
            100                 105                 110

Gly Gln Gly Thr Leu Val Thr Val Ser Ser
        115                 120

<210> SEQ ID NO 7
<211> LENGTH: 339
<212> TYPE: DNA
<213> ORGANISM: Artificial Sequence
<220> FEATURE:
<223> OTHER INFORMATION: synthesized

<400> SEQUENCE: 7
gacatccaga tgacccagtc tccatcctcc ctgtctgcat ctgtaggaga cagagtcacc      60
atcacttgcc agtccagtca gagtgtttat aacaacaacg acttagcctg gtatcagcag     120
aaaccaggga agttcctaa gctcctgatc tattatgctt ccactctggc atctggggtc     180
ccatctcggt tcagtggcag tggatctggg acagatttca ctctcaccat cagcagcctg     240
cagcctgaag atgttgcaac ttattactgt gcaggcggtt atgatacgga tggtcttgat     300
acgtttgctt tcggcggagg gaccaaggtg gagatcaaa                            339

<210> SEQ ID NO 8
<211> LENGTH: 113
<212> TYPE: PRT
<213> ORGANISM: Artificial Sequence
<220> FEATURE:
<223> OTHER INFORMATION: synthesized

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asp Leu Ala Trp Tyr Gln Gln Lys Pro Gly Lys Val Pro Lys Leu
        35                  40                  45

Leu Ile Tyr Tyr Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Asp Thr
                85                  90                  95

Asp Gly Leu Asp Thr Phe Ala Phe Gly Gly Gly Thr Lys Val Glu Ile
            100                 105                 110

Lys

<210> SEQ ID NO 9
<211> LENGTH: 345
<212> TYPE: DNA
<213> ORGANISM: Artificial Sequence
<220> FEATURE:
<223> OTHER INFORMATION: synthesized

<400> SEQUENCE: 9

```
gaggtgcagc tggtggagtc tgggggaggc ttggtccagc ctgggggtc cctgagactc      60
tcctgtactg cctctggatt ctccctcagt agctatgcaa tgagctgggt ccgccaggct    120
ccagggaggg gctggagtg atcggaatc atttatgcta gtggtagcac atactacgcg      180
agctcggcga aaggcagatt caccatctcc aaagacaata ccaagaacac ggtggatctt    240
caaatgaaca gcctgagagc cgaggacacg gctgtgtatt actgtgcgag aatttatgac    300
ggcatggacc tctggggcca gggaactctg gttaccgtct cttca                    345
```

<210> SEQ ID NO 10
<211> LENGTH: 115
<212> TYPE: PRT
<213> ORGANISM: Artificial Sequence
<220> FEATURE:
<223> OTHER INFORMATION: synthesized

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ser Trp Val Arg Gln Ala Pro Gly Arg Gly Leu Glu Trp Ile
        35                  40                  45

Gly Ile Ile Tyr Ala Ser Gly Ser Thr Tyr Tyr Ala Ser Ser Ala Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Ile Tyr Asp Gly Met Asp Leu Trp Gly Gln Gly Thr Leu Val Thr
            100                 105                 110

Val Ser Ser
        115

<210> SEQ ID NO 11
<211> LENGTH: 321
<212> TYPE: DNA
<213> ORGANISM: Artificial Sequence
<220> FEATURE:
<223> OTHER INFORMATION: synthesized

<400> SEQUENCE: 11

```
gacatccaga tgacccagtc tccatcctcc ctgtctgcat ctgtaggaga cagagtcacc      60
atcaattgcc aggccagtca gaacatttac agctacttat cctggtatca gcagaaacca    120
gggaaagttc ctaagcgcct gatctatctg gcatctactc tggcatctgg ggtcccatct    180
cggttcagtg gcagtggatc tgggacagat tacactctca ccatcagcag cctgcagcct    240
gaagatgttg caacttatta ctgtcaaagc aattataacg gtaattatgg tttcggcgga    300
gggaccaagg tggagatcaa a                                              321
```

<210> SEQ ID NO 12
<211> LENGTH: 107
<212> TYPE: PRT
<213> ORGANISM: Artificial Sequence
<220> FEATURE:
<223> OTHER INFORMATION: synthesized

<400> SEQUENCE: 12

```
Asp Ile Gln Met Thr Gln Ser Pro Ser Leu Ser Ala Ser Val Gly
1               5                   10                  15

Asp Arg Val Thr Ile Asn Cys Gln Ala Ser Gln Asn Ile Tyr Ser Tyr
            20                  25                  30

Leu Ser Trp Tyr Gln Gln Lys Pro Gly Lys Val Pro Lys Arg Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Ser Asn Tyr Asn Gly Asn Tyr
                85                  90                  95

Gly Phe Gly Gly Gly Thr Lys Val Glu Ile Lys
            100                 105
```

<210> SEQ ID NO 13
<211> LENGTH: 345
<212> TYPE: DNA
<213> ORGANISM: Artificial Sequence
<220> FEATURE:
<223> OTHER INFORMATION: synthesized

<400> SEQUENCE: 13

```
cagtcggtgg aggagtctgg gggaggcttg gtccagcctg ggggggtccct gagactctcc    60 tgtacagcct ctggaatcga ccttaatacc tacgacatga tctgggtccg ccaggctcca   120 ggcaagggggc tagagtgggt tggaatcatt acttatagtg gtagtagata ctacgcgaac   180
tgggcgaaag gccgattcac catctccaaa gacaatacca agaacacggt gtatctgcaa   240
atgaacagcc tgagagctga ggacacggct gtgtattact gtgccagaga ttatatgagt   300 ggttccccact tgtggggcca gggaaccctg gtcaccgtct ctagt                  345
```

<210> SEQ ID NO 14
<211> LENGTH: 115
<212> TYPE: PRT
<213> ORGANISM: Artificial Sequence
<220> FEATURE:
<223> OTHER INFORMATION: synthesized

<400> SEQUENCE: 14

```
Gln Ser Val Glu Glu Ser Gly Gly Gly Leu Val Gln Pro Gly Gly Ser
1               5                   10                  15

Leu Arg Leu Ser Cys Thr Ala Ser Gly Ile Asp Leu Asn Thr Tyr Asp
            20                  25                  30

Met Ile Trp Val Arg Gln Ala Pro Gly Lys Gly Leu Glu Trp Val Gly
        35                  40                  45

Ile Ile Thr Tyr Ser Gly Ser Arg Tyr Tyr Ala Asn Trp Ala Lys Gly
    50                  55                  60

Arg Phe Thr Ile Ser Lys Asp Asn Thr Lys Asn Thr Val Tyr Leu Gln
65                  70                  75                  80

Met Asn Ser Leu Arg Ala Glu Asp Thr Ala Val Tyr Tyr Cys Ala Arg
```

```
                    85                  90                  95
Asp Tyr Met Ser Gly Ser His Leu Trp Gly Gln Gly Thr Leu Val Thr
                100                 105                 110

Val Ser Ser
        115

<210> SEQ ID NO 15
<211> LENGTH: 330
<212> TYPE: DNA
<213> ORGANISM: Artificial Sequence
<220> FEATURE:
<223> OTHER INFORMATION: synthesized

<400> SEQUENCE: 15
gcctatgata tgacccagtc tccatcttcc gtgtctgcat ctgtaggaga cagagtcacc    60
atcaagtgtc aggccagtga ggacatttat agcttcttgg cctggtatca gcagaaacca   120
gggaaagccc ctaagctcct gatccattct gcatcctctc tggcatctgg ggtcccatca   180
aggttcagcg gcagtggatc tgggacagat ttcactctca ccatcagcag cctgcagcct   240
gaagattttg caacttacta ttgtcaacag ggttatggta aaaataatgt tgataatgct   300
ttcggcggag ggaccaaggt ggagatcaaa                                    330

<210> SEQ ID NO 16
<211> LENGTH: 110
<212> TYPE: PRT
<213> ORGANISM: Artificial Sequence
<220> FEATURE:
<223> OTHER INFORMATION: synthesized

<400> SEQUENCE: 16

Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys
                100                 105                 110

<210> SEQ ID NO 17
<211> LENGTH: 375
<212> TYPE: DNA
<213> ORGANISM: Artificial Sequence
<220> FEATURE:
<223> OTHER INFORMATION: synthesized

<400> SEQUENCE: 17
caggtgcaat tggtggaaag cggaggggga ctggtgcagc cggggggaag tctgaagctg    60
tcctgtgccg ccagcggctt taccttcaac aagtacgcca tgaattgggt ccgacaggcc   120
ccagggaaag gctggaatg gtggcacgg attcggtcca agtacaacaa ctacgccacc   180
tactacgctg actccgtgaa ggacagattc accatcagcg ggacgactc taagaacacc   240
```

```
gcctatctgc agatgaacaa cctgaaaacc gaggatacag ctgtgtacta ttgtgtgcgg    300
cacggcaact tcggcaactc ctacatctcc tactgggcct attggggaca gggaacactg    360
gtcaccgtgt ctagc                                                     375
```

```
<210> SEQ ID NO 18
<211> LENGTH: 125
<212> TYPE: PRT
<213> ORGANISM: Artificial Sequence
<220> FEATURE:
<223> OTHER INFORMATION: synthesized

<400> SEQUENCE: 18
```

```
Gln Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125
```

```
<210> SEQ ID NO 19
<211> LENGTH: 333
<212> TYPE: DNA
<213> ORGANISM: Artificial Sequence
<220> FEATURE:
<223> OTHER INFORMATION: synthesized

<400> SEQUENCE: 19
cagaccgtgg tcacccagga accttccctg accgtctccc caggcggcac cgtgaccctg    60
acctgtggct cctctaccgg cgctgtgacc tccggcaact accctaactg ggtgcagcag    120
aaacccggac aggctcctag aggcctgatc ggcggcacca gtttctggc ccctggcacc    180 cctgccagat tctccggctc cctgctggga ggcaaggccg ctctgaccct gtctggcgtg    240
cagcctgagg acgaggccga gtactactgt gtgctgtggt actccaacag atgggtgttc    300
ggaggcggca aaagctgac cgtgctgtcc tcg                                  333
```

```
<210> SEQ ID NO 20
<211> LENGTH: 111
<212> TYPE: PRT
<213> ORGANISM: Artificial Sequence
<220> FEATURE:
<223> OTHER INFORMATION: synthesized

<400> SEQUENCE: 20
```

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
```

```
                35                  40                  45
Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
                 85                  90                  95

Arg Trp Val Phe Gly Gly Gly Thr Lys Leu Thr Val Leu Ser Ser
            100                 105                 110

<210> SEQ ID NO 21
<211> LENGTH: 360
<212> TYPE: DNA
<213> ORGANISM: Artificial Sequence
<220> FEATURE:
<223> OTHER INFORMATION: synthesized

<400> SEQUENCE: 21
gaggtgcagc tggtggagtc tgggggaggc ttggtccagc ctggggggtc cctgagactc      60
tcctgtgcag cctctggatt caccatcagt accaatgcaa tgagctgggt ccgccaggct     120
ccagggaagg ggctggagtg gatcggagtc attactggtc gtgatatcac atactacgcg     180
agctgggcga aaggcagatt caccatctcc agagacaatt ccaagaacac gctgtatctt     240
caaatgaaca gcctgagagc cgaggacacg gctgtgtatt actgtgcgcg cgacggtgga     300
tcatctgcta ttactagtaa caacatttgg ggccaaggaa ctctggtcac cgtttcttca     360

<210> SEQ ID NO 22
<211> LENGTH: 120
<212> TYPE: PRT
<213> ORGANISM: Artificial Sequence
<220> FEATURE:
<223> OTHER INFORMATION: synthesized

<400> SEQUENCE: 22

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Ser Thr Asn
             20                  25                  30

Ala Met Ser Trp Val Arg Gln Ala Pro Gly Lys Gly Leu Glu Trp Ile
         35                  40                  45

Gly Val Ile Thr Gly Arg Asp Ile Thr Tyr Tyr Ala Ser Trp Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Gly Gly Ser Ser Ala Ile Thr Ser Asn Asn Ile Trp Gly Gln
            100                 105                 110

Gly Thr Leu Val Thr Val Ser Ser
            115                 120

<210> SEQ ID NO 23
<211> LENGTH: 336
<212> TYPE: DNA
<213> ORGANISM: Artificial Sequence
<220> FEATURE:
<223> OTHER INFORMATION: synthesized

<400> SEQUENCE: 23
```

```
gacgtcgtga tgacccagtc tccttccacc ctgtctgcat ctgtaggaga cagagtcacc    60
atcaattgcc aagccagtga gagcattagc agttggttag cctggtatca gcagaaacca   120
gggaaagccc ctaagctcct gatctatgaa gcatccaaac tggcatctgg ggtcccatca   180
aggttcagcg gcagtggatc tgggacagag ttcactctca ccatcagcag cctgcagcct   240
gatgattttg caacttatta ctgccaaggc tatttttatt ttattagtcg tacttatgta   300
aattctttcg gcggagggac caaggtggag atcaaa                              336
```

<210> SEQ ID NO 24
<211> LENGTH: 112
<212> TYPE: PRT
<213> ORGANISM: Artificial Sequence
<220> FEATURE:
<223> OTHER INFORMATION: synthesized

<400> SEQUENCE: 24

```
Asp Val Val Met Thr Gln Ser Pro Ser Thr Leu Ser Ala Ser Val Gly
 1               5                  10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Gly Thr Lys Val Glu Ile Lys
            100                 105                 110
```

<210> SEQ ID NO 25
<211> LENGTH: 360
<212> TYPE: DNA
<213> ORGANISM: Artificial Sequence
<220> FEATURE:
<223> OTHER INFORMATION: synthesized

<400> SEQUENCE: 25

```
gaggtgcagc tggtggagtc tgggggaggc ttggtccagc ctggggggtc cctgagactc    60
tcctgtacgg cctctggatt caccatcagt agcaatgcaa tgagctgggt ccgccaggct   120
ccagggaagg ggctggagtg gatcggagtc attactggtc gtgatatcac atactacgcg   180
agctgggcga aaggcagatt caccatctcc aaagacacct ccaagaacac ggtggatctt   240
caaatgaaca gcctgagagc cgaggacacg gctgtgtatt actgtgcgcg cgacggtgga   300
tcatctgcta ttactagtaa caacatttgg ggccaaggaa ctctggtcac cgtttcttca   360
```

<210> SEQ ID NO 26
<211> LENGTH: 120
<212> TYPE: PRT
<213> ORGANISM: Artificial Sequence
<220> FEATURE:
<223> OTHER INFORMATION: synthesized

<400> SEQUENCE: 26

```
Glu Val Gln Leu Val Glu Ser Gly Gly Gly Leu Val Gln Pro Gly Gly
 1               5                  10                  15
```

Ser Leu Arg Leu Ser Cys Thr Ala Ser Gly Phe Thr Ile Ser Ser Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Lys Asp Thr Ser Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Thr Ser Asn Asn Ile Trp Gly Gln
            100                 105                 110

Gly Thr Leu Val Thr Val Ser Ser
            115                 120

<210> SEQ ID NO 27
<211> LENGTH: 336
<212> TYPE: DNA
<213> ORGANISM: Artificial Sequence
<220> FEATURE:
<223> OTHER INFORMATION: synthesized

<400> SEQUENCE: 27
gacatccaga tgacccagtc tccttccacc ctgtctgcat ctgtaggaga cagagtcacc    60
atcacttgcc aagccagtga gagcattagc agttggttag cctggtatca gcagaaacca   120
gggaaagccc ctaagctcct gatctatgaa gcatccaaac tggcatctgg ggtcccatca   180
aggttcagcg gcagtggatc tgggacagag ttcactctca ccatcagcag cctgcagcct   240
gatgattttg caacttatta ctgccaaggc tattttatt ttattagtcg tagttatgta   300
aatgctttcg gcggagggac caaggtggag atcaaa                            336

<210> SEQ ID NO 28
<211> LENGTH: 112
<212> TYPE: PRT
<213> ORGANISM: Artificial Sequence
<220> FEATURE:
<223> OTHER INFORMATION: synthesized

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Ser Tyr Val Asn Ala Phe Gly Gly Gly Thr Lys Val Glu Ile Lys
            100                 105                 110

<210> SEQ ID NO 29
<211> LENGTH: 360
<212> TYPE: DNA
<213> ORGANISM: Artificial Sequence
<220> FEATURE:
<223> OTHER INFORMATION: synthesized

<400> SEQUENCE: 29

```
gaggtgcagc tggtggagtc tgggggaggc ttggtccagc ctgggggtc cctgagactc      60
tcctgtgcag cctctggaat cgacctcagt agcaatgcaa tgagctgggt ccgccaggct    120
ccagggaagg ggctggagtg gatcggagtc attactggtc gtgatatcac atactacgcg    180
agctgggcga aaggcagatt caccatctcc agagacaatt ccaagaacac gctgtatctt    240
caaatgaaca gcctgagagc cgaggacacg gctgtgtatt actgtgcgcg cgacggtgga    300
tcatctgcta ttaatagtaa gaacatttgg ggccaaggaa ctctggtcac cgtttcttca    360
```

<210> SEQ ID NO 30
<211> LENGTH: 120
<212> TYPE: PRT
<213> ORGANISM: Artificial Sequence
<220> FEATURE:
<223> OTHER INFORMATION: synthesized

<400> SEQUENCE: 30

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Ile Asp Leu Ser Ser Asn
            20                  25                  30
Ala Met Ser Trp Val Arg Gln Ala Pro Gly Lys Gly Leu Glu Trp Ile
        35                  40                  45
Gly Val Ile Thr Gly Arg Asp Ile Thr Tyr Tyr Ala Ser Trp Ala Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Asp Gly Gly Ser Ser Ala Ile Asn Ser Lys Asn Ile Trp Gly Gln
            100                 105                 110
Gly Thr Leu Val Thr Val Ser Ser
        115                 120
```

<210> SEQ ID NO 31
<211> LENGTH: 360
<212> TYPE: DNA
<213> ORGANISM: Artificial Sequence
<220> FEATURE:
<223> OTHER INFORMATION: synthesized

<400> SEQUENCE: 31

```
gaggtgcagc tggtggagtc tgggggaggc ttggtccagc ctggagggtc cctgagactc      60
tcctgtacgg cctctggaat cgacctcagt agcaatgcaa tgagctgggt ccgccaggct    120
ccagggaaag ggctggagtg gatcggagtc attactggtc gtgatatcac atactacgcg    180
agctgggcga aaggcagatt caccatctcc aaagacacct ccaagaacac ggtggatctt    240
caaatgaaca gcctgagagc cgaggacacg gctgtgtatt actgtgcgcg cgacggtgga    300
tcatctgcta ttaatagtaa gaacatttgg ggccaaggaa ctctggtcac cgtttcttca    360
```

<210> SEQ ID NO 32
<211> LENGTH: 120
<212> TYPE: PRT
<213> ORGANISM: Artificial Sequence
<220> FEATURE:

<223> OTHER INFORMATION: synthesized

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Thr Ala Ser Gly Ile Asp Leu Ser Ser Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Lys Asp Thr Ser Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Asn Ser Lys Asn Ile Trp Gly Gln
            100                 105                 110

Gly Thr Leu Val Thr Val Ser Ser
        115                 120

<210> SEQ ID NO 33
<211> LENGTH: 336
<212> TYPE: DNA
<213> ORGANISM: Artificial Sequence
<220> FEATURE:
<223> OTHER INFORMATION: synthesized

<400> SEQUENCE: 33
gacatccaga tgacccagtc tccttccacc ctgtctgcat ctgtaggaga cagagtcacc      60
atcacttgcc aagccagtga gagcattagc agttggttag cctggtatca gcagaaacca     120
gggaaagccc ctaagctcct gatctatgaa gcatccaaac tggcatctgg ggtcccatca     180
aggttcagcg gcagtggatc tgggacagag ttcactctca ccatcagcag cctgcagcct     240
gatgattttg caacttatta ctgccaaggc tatttttatt ttattagtcg tacttatgta     300
aatgctttcg gcggagggac caaggtggag atcaaa                               336

<210> SEQ ID NO 34
<211> LENGTH: 112
<212> TYPE: PRT
<213> ORGANISM: Artificial Sequence
<220> FEATURE:
<223> OTHER INFORMATION: synthesized

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ala Phe Gly Gly Gly Thr Lys Val Glu Ile Lys

<210> SEQ ID NO 35
<211> LENGTH: 354
<212> TYPE: DNA
<213> ORGANISM: Artificial Sequence
<220> FEATURE:
<223> OTHER INFORMATION: synthesized

<400> SEQUENCE: 35

```
gaggtgaagc tggatgagac tggaggaggc ttggtgcaac ctgggaggcc catgaaactc      60
tcctgtgttg cctctggatt cactttagt gactactgga tgaactgggt ccgccagtct     120
ccagagaaag gactggagtg ggtagcacaa attagaaaca aaccttataa ttatgaaaca     180
tattattcag attctgtgaa aggcagattc accatctcaa gagatgattc caaaagtagt     240
gtctacctgc aaatgaacaa cttaagagtt gaagacatgg gtatctatta ctgtacgggt     300
tcttactatg gtatggacta ctggggtcaa ggaacctcag tcaccgtctc ctca          354
```

<210> SEQ ID NO 36
<211> LENGTH: 118
<212> TYPE: PRT
<213> ORGANISM: Artificial Sequence
<220> FEATURE:
<223> OTHER INFORMATION: synthesized

<400> SEQUENCE: 36

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser
        115

<210> SEQ ID NO 37
<211> LENGTH: 336
<212> TYPE: DNA
<213> ORGANISM: Artificial Sequence
<220> FEATURE:
<223> OTHER INFORMATION: synthesized

<400> SEQUENCE: 37

```
gatgtcgtga tgacccaaac tccactctcc ctgcctgtca gtcttggaga tcaagcctcc      60
atctcttgca gatctagtca gagccttgta cacagtaatg aaacacctta tttacgttgg     120
tacctgcaga agccaggcca gtctccaaag gtcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tggacgttcg gtggaggcac caagctggaa atcaaa                              336
```

<210> SEQ ID NO 38
<211> LENGTH: 112
<212> TYPE: PRT
<213> ORGANISM: Artificial Sequence
<220> FEATURE:
<223> OTHER INFORMATION: synthesized

<400> SEQUENCE: 38

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 39
<211> LENGTH: 348
<212> TYPE: DNA
<213> ORGANISM: Artificial Sequence
<220> FEATURE:
<223> OTHER INFORMATION: synthesized

<400> SEQUENCE: 39
gatgtgcagc ttcaggagtc gggacctagc ctggtgaaac cttctcagtc tctgtccctc     60
acctgcactg tcactggcta ctcaatcacc agtgattttg cctggaactg gattcggcag    120
tttccaggaa acaagctgga gtggatgggc tacataagtt atagtggtaa cactaggtac    180
aacccatctc tcaaaagtcg aatctctatc actcgcgaca catccaagaa ccaattcttc    240
ctgcagttga actctgtgac tattgaggac acagccacat attactgtgt aacggcggga    300
cgcgggtttc cttattgggg ccaagggact ctggtcactg tctctgca                 348

<210> SEQ ID NO 40
<211> LENGTH: 116
<212> TYPE: PRT
<213> ORGANISM: Artificial Sequence
<220> FEATURE:
<223> OTHER INFORMATION: synthesized

<400> SEQUENCE: 40

Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

```
Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Thr Leu Val
            100                 105                 110

Thr Val Ser Ala
        115

<210> SEQ ID NO 41
<211> LENGTH: 321
<212> TYPE: DNA
<213> ORGANISM: Artificial Sequence
<220> FEATURE:
<223> OTHER INFORMATION: synthesized

<400> SEQUENCE: 41
gacatcctga tgacccaatc tccatcctcc atgtctgtat ctctgggaga cacagtcagc    60
atcacttgcc attcaagtca ggacattaac agtaatatag ggtggttgca gcagagacca   120
gggaaatcat ttaagggcct gatctatcat ggaaccaact tggacgatga agttccatca   180
aggttcagtg gcagtggatc tggagccgat tattctctca ccatcagcag cctggaatct   240
gaagattttg cagactatta ctgtgtacag tatgctcagt ttccgtggac gttcggtgga   300
ggcaccaagc tggaaatcaa a                                             321

<210> SEQ ID NO 42
<211> LENGTH: 107
<212> TYPE: PRT
<213> ORGANISM: Artificial Sequence
<220> FEATURE:
<223> OTHER INFORMATION: synthesized

<400> SEQUENCE: 42

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys
            100                 105

<210> SEQ ID NO 43
<211> LENGTH: 363
<212> TYPE: DNA
<213> ORGANISM: Artificial Sequence
<220> FEATURE:
<223> OTHER INFORMATION: synthesized

<400> SEQUENCE: 43
gaggtgcagc tggtgcagtc tggagcagag gtgaagaaac caggagagtc tctgaagatc    60
tcctgtaagg gttctggata cagctttagc agttcatgga tcggctgggt gcgccaggca   120
cctgggaaag gcctggaatg gatggggatc atctatcctg atgactctga taccagatac   180
agtccatcct tccaaggcca ggtcaccatc tcagccgaca gtccatcag gactgcctac   240
```

```
ctgcagtgga gtagcctgaa ggcctcggac accgctatgt attactgtgc gagacatgtt      300
actatgattt gggagttat tattgacttc tggggccagg gaaccctggt caccgtctcc      360
tca                                                                     363
```

<210> SEQ ID NO 44
<211> LENGTH: 121
<212> TYPE: PRT
<213> ORGANISM: Artificial Sequence
<220> FEATURE:
<223> OTHER INFORMATION: synthesized

<400> SEQUENCE: 44

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Ser
            20                  25                  30

Trp Ile Gly Trp Val Arg Gln Ala Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Ile Trp Gly Val Ile Ile Asp Phe Trp Gly
            100                 105                 110

Gln Gly Thr Leu Val Thr Val Ser Ser
        115                 120
```

<210> SEQ ID NO 45
<211> LENGTH: 321
<212> TYPE: DNA
<213> ORGANISM: Artificial Sequence
<220> FEATURE:
<223> OTHER INFORMATION: synthesized

<400> SEQUENCE: 45

```
gccatccagt tgacccagtc tccatcctcc ctgtctgcat ctgtaggaga cagagtcacc       60
atcacttgcc gggcaagtca gggcattagc agtgctttag cctggtatca gcagaaacca      120
gggaaagctc ctaagctcct gatctatgat gcctccagtt tggaaagtgg ggtcccatca      180
aggttcagcg gcagtggatc tgggacagat ttcactctca ccatcagcag cctgcagcct      240
gaagattttg caacttatta ctgtcaacag tttaatagtt acccattcac tttcggccct      300
gggaccaaag tggatatcaa a                                                 321
```

<210> SEQ ID NO 46
<211> LENGTH: 107
<212> TYPE: PRT
<213> ORGANISM: Artificial Sequence
<220> FEATURE:
<223> OTHER INFORMATION: synthesized

<400> SEQUENCE: 46

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30
```

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Phe
                 85                  90                  95

Thr Phe Gly Pro Gly Thr Lys Val Asp Ile Lys
            100                 105

<210> SEQ ID NO 47
<211> LENGTH: 987
<212> TYPE: DNA
<213> ORGANISM: Artificial Sequence
<220> FEATURE:
<223> OTHER INFORMATION: synthesized

<400> SEQUENCE: 47
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaagc cgcggggggca     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcgcggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc tccgggt                                        987

<210> SEQ ID NO 48
<211> LENGTH: 329
<212> TYPE: PRT
<213> ORGANISM: Artificial Sequence
<220> FEATURE:
<223> OTHER INFORMATION: synthesized

<400> SEQUENCE: 48

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser

```
                 50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
                115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 49
<211> LENGTH: 321
<212> TYPE: DNA
<213> ORGANISM: Artificial Sequence
<220> FEATURE:
<223> OTHER INFORMATION: synthesized

<400> SEQUENCE: 49
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 50
<211> LENGTH: 107
<212> TYPE: PRT
```

<213> ORGANISM: Artificial Sequence
<220> FEATURE:
<223> OTHER INFORMATION: synthesized

<400> SEQUENCE: 50

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 51
<211> LENGTH: 2913
<212> TYPE: DNA
<213> ORGANISM: Artificial Sequence
<220> FEATURE:
<223> OTHER INFORMATION: synthesized

<400> SEQUENCE: 51

| | | | | | |
|---|---|---|---|---|---|
| gacatccaga | tgacccagtc | tccatcctcc | ctgtctgcat | ctgtaggaga | cagagtcacc | 60 |
| atcacttgcc | agtccagtca | gagtgtttat | aacaacaacg | acttagcctg | gtatcagcag | 120 |
| aaaccaggga | aagttcctaa | gctcctgatc | tattatgctt | ccactctggc | atctggggtc | 180 |
| ccatctcggt | tcagtggcag | tggatctggg | acagatttca | ctctcaccat | cagcagcctg | 240 |
| cagcctgaag | atgttgcaac | ttattactgt | gcaggcggtt | atgatacgga | tggtcttgat | 300 |
| acgtttgctt | tcggcggagg | gaccaaggtg | gagatcaaag | gcggtggcgg | tagtggggga | 360 |
| ggcggttctg | gcggcggagg | gtccggcggt | ggaggatcag | aggtgcagct | gttggagtct | 420 |
| gggggaggct | tggtacagcc | tggggggtcc | ctgagactct | cctgtgcagc | ctctggattc | 480 |
| accatcagtc | gctaccacat | gacttgggtc | cgccaggctc | cagggaaggg | gctggagtgg | 540 |
| atcggacata | tttatgttaa | taatgatgac | acagactacg | cgagctccgc | gaaaggccgg | 600 |
| ttcaccatct | ccagagacaa | ttccaagaac | acgctgtatc | tgcaaatgaa | cagcctgaga | 660 |
| gccgaggaca | cggccaccta | tttctgtgcg | agattggatg | ttggtggtgg | tggtgcttat | 720 |
| attgggggaca | tctggggcca | gggaactctg | gttaccgtct | cttcaggcgg | tggagggtcc | 780 |
| ggcggtggtg | gatcccagtc | ggtggaggag | tctgggggag | gcttggtcca | gcctggggg | 840 |
| tccctgagac | tctcctgtac | agcctctgga | atcgacctta | ataccacgga | catgatctgg | 900 |
| gtccgccagg | ctccaggcaa | ggggctagag | tgggttggaa | tcattactta | tagtggtagt | 960 |
| agatactacg | cgaactgggc | gaaaggccga | ttcaccatct | ccaaagacaa | taccaagaac | 1020 |
| acggtgtatc | tgcaaatgaa | cagcctgaga | gctgaggaca | cggctgtgta | ttactgtgcc | 1080 |
| agagattata | tgagtggttc | ccacttgtgg | ggccagggaa | ccctggtcac | cgtctctagt | 1140 |
| gctagcacca | aggccccatc | ggtcttcccc | ctggcaccct | cctccaagag | cacctctggg | 1200 |
| ggcacagcgg | ccctgggctg | cctggtcaag | gactacttcc | ccgaaccggt | gacggtgtcg | 1260 |

-continued

```
tggaactcag gcgccctgac cagcggcgtg cacaccttcc cggctgtcct acagtcctca    1320
ggactctact ccctcagcag cgtggtgacc gtgccctcca gcagcttggg cacccagacc    1380
tacatctgca acgtgaatca caagcccagc aacaccaagg tggacaagag agttgagccc    1440
aaatcttgtg acaaaactca cacatgccca ccgtgcccag cacctgaagc cgcggggggca   1500 ccgtcagtct tcctcttccc cccaaaaccc aaggacaccc tcatgatctc ccggacccct    1560
gaggtcacat gcgtggtggt ggacgtgagc cacgaagacc ctgaggtcaa gttcaactgg    1620
tacgtggacg gcgtggaggt gcataatgcc aagacaaagc cgcgggagga gcagtacaac    1680
agcacgtacc gtgtggtcag cgtcctcacc gtcctgcacc aggactggct gaatggcaag    1740
gagtacaagt gcgcggtctc caacaaagcc ctcccagccc ccatcgagaa aaccatctcc    1800
aaagccaaag gcagccccg  agaaccacag gtgtataccc tgcccccatc ccgggatgag    1860
ctgaccaaga accaggtcag cctgacctgc ctggtcaaag gcttctatcc cagcgacatc    1920
gccgtggagt gggagagcaa tgggcagccg gagaacaact acaagaccac gcctcccgtg    1980
ctggactccg acggctcctt cttcctctat agcaagctca ccgtggacaa gagcaggtgg    2040
cagcagggga acgtcttctc atgctccgtg atgcatgagg ctctgcacaa ccactacacg    2100
cagaagagcc tctccctgtc tccgggtggc ggtggagggt ccggcggtgg tggatccgag    2160
gtgcagctgg tggagtctgg gggaggcttg gtccagcctg gggggtccct gagactctcc    2220
tgtgcagcct ctggattcac catcagtacc aatgcaatga ctgggtccg  ccaggctcca    2280 gggaagggc  tggagtggat cggagtcatt actggtcgtg atatcacata ctacgcgagc    2340
tgggcgaaag gcagattcac catctccaga gacaattcca gaacacgct  gtatcttcaa    2400 atgaacagcc tgagagccga ggacacggct gtgtattact gtgcgcgcga cggtggatca    2460
tctgctatta ctagtaacaa catttggggc caaggaactc tggtcaccgt ttcttcaggc    2520
ggtggcggta gtgggggagg cggttctggc ggcgagggt  ccggcggtgg aggatcagac    2580
gtcgtgatga cccagtctcc ttccaccctg tctgcatctg taggagacag agtcaccatc    2640
aattgccaag ccagtgagag cattagcagt tggttagcct ggtatcagca gaaaccaggg    2700
aaagccccta agctcctgat ctatgaagca tccaaactgg catctggggt cccatcaagg    2760
ttcagcggca gtggatctgg gacagagttc actctcacca tcagcagcct gcagcctgat    2820
gattttgcaa cttattactg ccaaggctat ttttatttta ttagtcgtac ttatgtaaat    2880
tctttcggcg agggaccaa  ggtggagatc aaa                                2913
```

<210> SEQ ID NO 52
<211> LENGTH: 831
<212> TYPE: PRT
<213> ORGANISM: Artificial Sequence
<220> FEATURE:
<223> OTHER INFORMATION: synthesized
<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asp Leu Ala Trp Tyr Gln Gln Lys Pro Gly Lys Val Pro Lys Leu
        35                  40                  45

Leu Ile Tyr Tyr Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
```

-continued

```
            65                  70                  75                  80
Gln Pro Glu Asp Val Ala Thr Tyr Tyr Cys Ala Gly Gly Tyr Asp Thr
                    85                  90                  95
Asp Gly Leu Asp Thr Phe Ala Phe Gly Gly Thr Lys Val Glu Ile
                100                 105                 110
Lys Gly Gly Gly Gly Ser Gly Gly Gly Ser Gly Gly Gly Ser
                115                 120                 125
Gly Gly Gly Gly Ser Glu Val Gln Leu Leu Glu Ser Gly Gly Gly Leu
                130                 135                 140
Val Gln Pro Gly Gly Ser Leu Arg Leu Ser Cys Ala Ala Ser Gly Phe
145                 150                 155                 160
Thr Ile Ser Arg Tyr His Met Thr Trp Val Arg Gln Ala Pro Gly Lys
                165                 170                 175
Gly Leu Glu Trp Ile Gly His Ile Tyr Val Asn Asn Asp Asp Thr Asp
                180                 185                 190
Tyr Ala Ser Ser Ala Lys Gly Arg Phe Thr Ile Ser Arg Asp Asn Ser
                195                 200                 205
Lys Asn Thr Leu Tyr Leu Gln Met Asn Ser Leu Arg Ala Glu Asp Thr
210                 215                 220
Ala Thr Tyr Phe Cys Ala Arg Leu Asp Val Gly Gly Gly Ala Tyr
225                 230                 235                 240
Ile Gly Asp Ile Trp Gly Gln Gly Thr Leu Val Thr Val Ser Ser Gly
                245                 250                 255
Gly Gly Gly Ser Gly Gly Gly Ser Gln Ser Val Glu Glu Ser Gly
                260                 265                 270
Gly Gly Leu Val Gln Pro Gly Gly Ser Leu Arg Leu Ser Cys Thr Ala
                275                 280                 285
Ser Gly Ile Asp Leu Asn Thr Tyr Asp Met Ile Trp Val Arg Gln Ala
                290                 295                 300
Pro Gly Lys Gly Leu Glu Trp Val Gly Ile Ile Thr Tyr Ser Gly Ser
305                 310                 315                 320
Arg Tyr Tyr Ala Asn Trp Ala Lys Gly Arg Phe Thr Ile Ser Lys Asp
                325                 330                 335
Asn Thr Lys Asn Thr Val Tyr Leu Gln Met Asn Ser Leu Arg Ala Glu
                340                 345                 350
Asp Thr Ala Val Tyr Tyr Cys Ala Arg Asp Tyr Met Ser Gly Ser His
                355                 360                 365
Leu Trp Gly Gln Gly Thr Leu Val Thr Val Ser Ser Ala Ser Thr Lys
370                 375                 380
Gly Pro Ser Val Phe Pro Leu Ala Pro Ser Ser Lys Ser Thr Ser Gly
385                 390                 395                 400
Gly Thr Ala Ala Leu Gly Cys Leu Val Lys Asp Tyr Phe Pro Glu Pro
                405                 410                 415
Val Thr Val Ser Trp Asn Ser Gly Ala Leu Thr Ser Gly Val His Thr
                420                 425                 430
Phe Pro Ala Val Leu Gln Ser Ser Gly Leu Tyr Ser Leu Ser Ser Val
                435                 440                 445
Val Thr Val Pro Ser Ser Leu Gly Thr Gln Thr Tyr Ile Cys Asn
                450                 455                 460
Val Asn His Lys Pro Ser Asn Thr Lys Val Asp Lys Arg Val Glu Pro
465                 470                 475                 480
Lys Ser Cys Asp Lys Thr His Thr Cys Pro Pro Cys Pro Ala Pro Glu
                485                 490                 495
```

Ala Ala Gly Ala Pro Ser Val Phe Leu Phe Pro Pro Lys Pro Lys Asp
                500                 505                 510

Thr Leu Met Ile Ser Arg Thr Pro Glu Val Thr Cys Val Val Val Asp
            515                 520                 525

Val Ser His Glu Asp Pro Glu Val Lys Phe Asn Trp Tyr Val Asp Gly
        530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Ala Val Ser Asn Lys Ala Leu Pro
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Ser Arg Asp Glu Leu Thr Lys Asn
610                 615                 620

Gln Val Ser Leu Thr Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
            690                 695                 700

Ser Leu Ser Pro Gly Gly Gly Gly Ser Gly Gly Gly Ser Asp
705                 710                 715                 720

Val Val Met Thr Gln Ser Pro Ser Thr Leu Ser Ala Ser Val Gly Asp
                725                 730                 735

Arg Val Thr Ile Asn Cys Gln Ala Ser Glu Ser Ile Ser Ser Trp Leu
            740                 745                 750

Ala Trp Tyr Gln Gln Lys Pro Gly Lys Ala Pro Lys Leu Leu Ile Tyr
        755                 760                 765

Glu Ala Ser Lys Leu Ala Ser Gly Val Pro Ser Arg Phe Ser Gly Ser
770                 775                 780

Gly Ser Gly Thr Glu Phe Thr Leu Thr Ile Ser Ser Leu Gln Pro Asp
785                 790                 795                 800

Asp Phe Ala Thr Tyr Tyr Cys Gln Gly Tyr Tyr Phe Ile Ser Arg
                805                 810                 815

Thr Tyr Val Asn Ser Phe Gly Gly Thr Lys Val Glu Ile Lys
            820                 825                 830

<210> SEQ ID NO 53
<211> LENGTH: 651
<212> TYPE: DNA
<213> ORGANISM: Artificial Sequence
<220> FEATURE:
<223> OTHER INFORMATION: synthesized

<400> SEQUENCE: 53
gcctatgata tgacccagtc tccatcttcc gtgtctgcat ctgtaggaga cagagtcacc      60
atcaagtgtc aggccagtga ggacatttat agcttcttgg cctggtatca gcagaaacca     120
gggaaagccc ctaagctcct gatccattct gcatcctctc tggcatctgg ggtcccatca     180

```
aggttcagcg gcagtggatc tgggacagat tcactctca ccatcagcag cctgcagcct      240
gaagattttg caacttacta ttgtcaacag ggttatggta aaaataatgt tgataatgct      300
ttcggcggag ggaccaaggt ggagatcaaa cgtacggtgg ctgcaccatc tgtcttcatc      360
ttcccgccat ctgatgagca gttgaaatct ggaactgcct ctgttgtgtg cctgctgaat      420
aacttctatc ccagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaag tctacgcctg cgaagtcacc      600
catcagggcc tgagctcgcc cgtcacaaag agcttcaaca ggggagagtg t              651
```

<210> SEQ ID NO 54
<211> LENGTH: 217
<212> TYPE: PRT
<213> ORGANISM: Artificial Sequence
<220> FEATURE:
<223> OTHER INFORMATION: synthesized

<400> SEQUENCE: 54

```
Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```